United States Patent [19]
Pedersen et al.

[11] Patent Number: 5,827,730
[45] Date of Patent: Oct. 27, 1998

[54] MUTANT DNA ENCODING INSULIN RECEPTOR SUBSTRATE 1

[75] Inventors: Oluf Pedersen, Holte; Christian Bjørbæk, Frederiksberg C; Kathrine Almind Frederiksen, København Ø, all of Denmark

[73] Assignee: Novo Nordisk A/S, Bagsvaerd, Denmark

[21] Appl. No.: 557,139

[22] PCT Filed: Jun. 10, 1994

[86] PCT No.: PCT/DK94/00227

§ 371 Date: Feb. 12, 1996

§ 102(e) Date: Feb. 12, 1996

[87] PCT Pub. No.: WO94/29345

PCT Pub. Date: Dec. 22, 1994

[30] Foreign Application Priority Data

Jun. 10, 1993 [DK] Denmark ................................ 0683/93
Aug. 9, 1993 [DK] Denmark ................................ 0915/93

[51] Int. Cl.⁶ ............................ C12N 15/00; C12N 5/00; C07K 1/00; C07H 21/04
[52] U.S. Cl. .................. 435/320.1; 435/325; 435/172.3; 800/2; 530/350; 536/23.1; 536/23.5
[58] Field of Search ............................ 800/2, DIG. 1–4; 435/325, 320.1; 536/23.1, 23.5

[56] References Cited

U.S. PATENT DOCUMENTS 5,162,215 11/1992 Bosselman et al. ................. 435/172.3
5,545,808 8/1996 Hew et al. ................................ 800/2
5,621,075 4/1997 Kahn et al. ............................ 530/350

FOREIGN PATENT DOCUMENTS

92/13083 8/1992 WIPO .

OTHER PUBLICATIONS

Shoelson et al. YMXM motifs of IRS–1 define substrate specificity of the insulin receptor kinase. PNAS, vol. 89, No. 6, pp. 2027–2031, Mar. 1992.
Pursel et al. Genetic engineering of livestock. Science, vol. 244, pp. 1281–1288, Jun. 16, 1989.
Houdebine, L. M. Production of pharmaceutical proteins from transgenic animals. J. of Biotechnology, vol. 34, pp. 269–287, 1994.
Dialog Information Services, file 155, Medline, Dialog accession No. 0852900, Medine accession No. 93239000.
Dialog Information Services, file 155, Medline, Dialog accession No. 08058050, Medline accession No. 92196050.
Dialog Information Services, file 155, Medline, Dialog accession No. 08231886, Medline accession No. 92369886.
Dialog Information Services, file 155, Medline, Dialog accession No. 0726027, Medline accession No. 90167273.
Dialog Information Services, file 155, Medline, Dialog accession No. 07601382, Medline accession No. 91120382.
Almind, K., et al., J. Clin. Invest., vol., 97, No. 11, pp. 1–7 (1996).
Dialog Information Services, file 155, Medline, Dialog accession No. 08680176, Medline accession No. 93390176.

*Primary Examiner*—Jasemine C. Chambers
*Assistant Examiner*—Deborah J. R. Clark
*Attorney, Agent, or Firm*—Steve T. Zelson, Esq.; Valeta Gregg, Esq.

[57] ABSTRACT

A DNA sequence encoding insulin receptor substrate 1 (IRS-1), the DNA sequence containing a mutation of at least one nucleotide, and the protein encoded by said DNA sequence.

6 Claims, 2 Drawing Sheets

MUTANT DNA ENCODING INSULIN RECEPTOR SUBSTRATE 1

CROSS-REFERENCE TO RELATED APPLICATIONS

This application is a continuation of PCT/DK94/00227 filed Jun. 10, 1994, which is incorporated herein by reference.

FIELD OF INVENTION

The present invention relates to a mutant DNA sequence encoding insulin receptor substrate 1, a method of detecting a mutation in the gene encoding insulin receptor substrate 1, as well as a diagnostic composition and a test kit for use in the method.

BACKGROUND OF THE INVENTION

Non-insulin-dependent diabetes mellitus (NIDDM) is a common endocrine disorder and a considerable body of evidence strongly suggests that genetic factors contribute to the pathogenesis (1). Studies of patients with overt NIDDM and of individuals at high risk of NIDDM reveal abnormalities of both insulin secretion and insulin action (2). However, a genetic defect at one or more loci in the cellular action of insulin and insulin-like growth factor 1 (IGF1) might well involve both the biochemical pathways of tissues that regulate insulin secretion and insulin sensitive hepatic and extrahepatic tissues that produce or extract glucose.

Although more than twenty different mutations of the insulin receptor gene have been reported in syndromes of severe insulin resistance frequently associated with the skin disorder acanthosis nigricans or ovarian hyperandrogenism (17), mutations in the insulin receptor molecule do not explain the genetic etiology of the common form of NIDDM.

The common form of late onset NIDDM is a heterogeneous disorder where at least two major defects contribute to the pathophysiology of the phenotype: insulin resistance and insulin deficiency (2). Most likely NIDDM is also polygenic and it is suggested that subsets of patients will display changes in various genes, in aggregate accounting for the inherited components of the disorder. The high cumulative risk of diabetes in offspring of NIDDM parents (30–50%) and the high concordance rate in identical twins (70–100%) underscore the significance of the genetic etiology of the disease (1).

Insulin initiates its cellular effects by binding to the a subunit of its tetrameric plasma membrane receptor (3). The kinase in the β subunit is thereby activated which in turn catalyzes the intramolecular autophosphorylation of specific tyrosine residues of the β subunit, further stimulating the tyrosine kinase activity of the receptor towards other protein substrates in the cascade of insulin action.

Recently, the first endogeneous substrate for the insulin receptor kinase (termed insulin receptor substrate 1, abbreviated to IRS-1) was cloned and sequenced (4–6). The complementary DNA sequence encodes a cytoplasmic, hydrophilic protein of a relative molecular mass between 165 and 185 kD (27,28) which contains multiple phosphorylation sites. Besides being a substrate for the insulin receptor kinase, IRS-1 is also phosphorylated following the activation of the IGF1 receptor kinase (16).

IRS-1 is barely detectable in cells expressing few insulin receptors, but is strongly detected in cells expressing high levels of receptors and weakly detected in cells expressing mutant receptors defective in biological signalling (27,28). IRS-1 is a unique molecule containing 20 tyrosine phosphorylation consensus sequences, 6 of which appear in YMXM (Tyr-Met-X-Met) motifs. Following insulin stimulated tyrosine phosphorylation of YMXM motifs in the IRS-1 molecule, the phosphorylated IRS-1 binds phosphatidylinositol 3-kinase (PI3-kinase) suggesting that IRS-1 acts as a multisite "docking" protein to bind signal proteins thereby linking the receptor kinase to insulin sensitive transporters and enzymes (7–15). The PI3-kinase is composed of at least two subunits including a 110 kDa catalytic subunit and a 85 kDa regulatory protein which contains src homology 2 domains that mediate protein-protein interactions by binding to phosphotyrosine residues in various proteins (7–15). Interestingly, it has been demonstrated that insulin causes the interaction between IRS-1 and PI-3 kinase via phosphorylated YMXM motifs of IRS-1 and src homology 2 domains of the 85 kDa regulatory subunit of PI-3 kinase. Moreover, overexpression of IRS-1 potentiates the activation of PI3-kinase in insulin stimulated cells, and tyrosyl phosphorylated IRS-1 or synthetic peptides containing phosphorylated YMXM motifs activate PI3-kinase in vitro. Besides being a substrate of the insulin receptor kinase, IRS-1 is also phosphorylated following the activation of the IGF1 receptor kinase (16). Hence, it has been suggested that IRS-1 by binding and regulating enzymes containing src homology 2 domains may play a critical role to select and differentiate the effects of insulin and IGF1 from those of other tyrosine kinases and to generate diversity and amplification of signal transmission into multiple intracellular pathways (7-16).

SUMMARY OF THE INVENTION

According to the present invention, it has surprisingly been found that a number of NIDDM patients carry mutations in the gene coding for IRS-1. It is at present assumed that one or more of the mutations may be involved in or associated with the etiology of NIDDM, and their presence may therefore be diagnostic for NIDDM and possibly also other disorders resulting from insulin resistance.

Accordingly, the present invention relates to a DNA construct comprising a DNA sequence encoding insulin receptor substrate 1 (IRS-1), the DNA sequence containing a mutation of at least one nucleotide, or comprising a fragment of the DNA sequence including said mutation.

It is at present assumed that mutation of the IRS-1 gene may be indicative of abnormalities significant for the development of NIDDM or other disorders. For instance, the mutation may give rise to the substitution of an amino acid in IRS-1 which may cause changes in the tertiary structure of IRS-1. Such changes may interfere with the normal interaction between the insulin or IGF-1 receptor kinase and one or more intracellular proteins regulating cellular metabolism and growth. These proteins typically have src homology 2 domains and include phosphatidyl inositol 3 kinase, GRB-2 and SHPTP-2 (vide M. F. White et al., *Exp. Clin. Endocrinol.* 101, Suppl. 2, 1993, pp. 98–99, in particular FIG. 1). Mutations may also interfere with the transcription or translation of the gene, or with the stability of the IRS-1 transcript. Alternatively, the mutation may be associated with (i.e. genetically linked with) the mutation which causes the disease.

In another aspect, the present invention relates to a living system containing a DNA construct of the invention and capable of expressing IRS-1 wherein at least one amino acid is substituted. The living system, which may comprise a cell or a multicellular organism containing the appropriate signal transduction pathway, may be used to screen for substances which have an effect on insulin or IGF-1 stimulated signal transduction in the system.

In a further aspect, the present invention relates to a method of detecting the presence of a mutation in the gene encoding IRS-1, the method comprising obtaining a biological sample from a subject and analysing the sample for a mutation of at least one nucleotide. Based on current knowledge, it is assumed that the present method may be used to diagnose predisposition to NIDDM in a subject as well as other disorders resulting from insulin resistance (such as android obesity, essential hypertension, dyslipidemia or atherosclerosis). Biological samples may, for instance, be obtained from blood, serum, plasma or tissue. The invention further relates to a diagnostic composition and a test kit for use in the method.

DETAILED DESCRIPTION OF THE INVENTION

Figure 1:
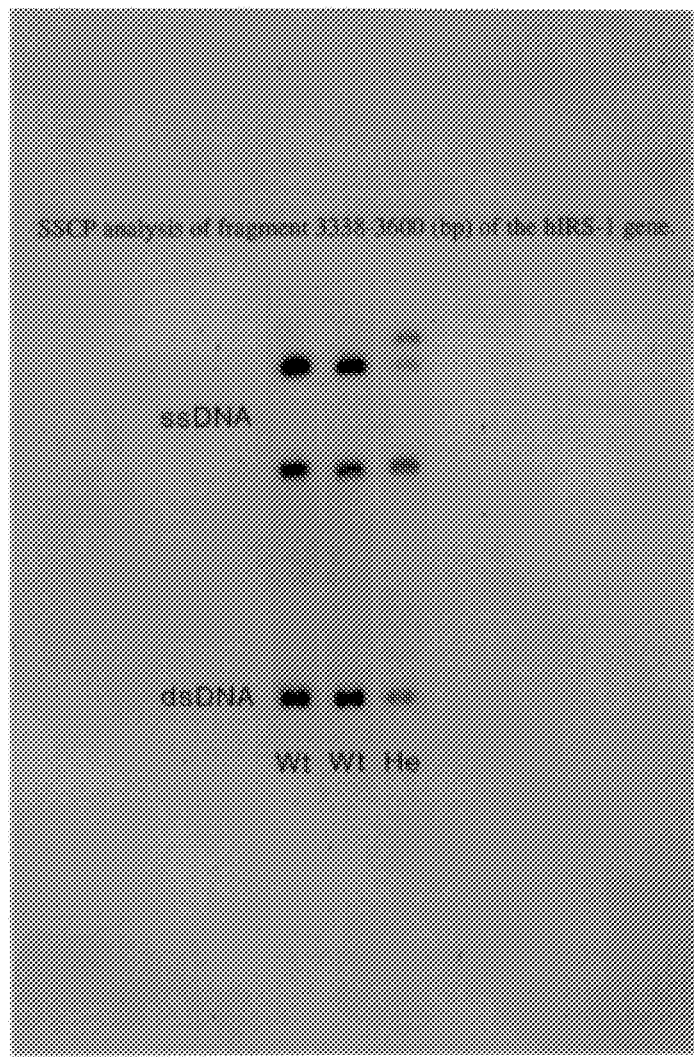
FIG. 1 shows mutation screening using single stranded conformation polymorphism technique (SSCP) of nucleotides 3338–3600 of the human insulin receptor substrate 1 (IRS-1 gene). The fragment was PCR-amplified from genomic DNA using specific oligonucleotide primers and $^{32}$P-labeled and subjected to nondenaturing gel electrophoresis as described in Methods. The autoradiogram shows the migration profiles of single stranded (ss DNA) as well as double stranded DNA (ds DNA). Lane 3 depicts the migration profile of an individual who is heterozygous (He) for the glycine$^{972}$ mutation. Lanes 1 and 2 show the migration profile for the corresponding wild type (Wt).

In particular, the present invention relates to a DNA construct comprising a DNA sequence encoding IRS-1 and containing a mutation giving rise to at least one amino acid substitution in the IRS-1 protein sequence. The mutation may for instance be located at a site where the amino acid substitution interferes with signal transduction through IRS-1, as such a mutation is most likely to be involved in disease etiology. An example of such a DNA sequence is one containing a mutation of G to A in the first position of codon 972 of the IRS-1 gene.

This mutation leads to substitution of glycine by arginine in position 972. The molecular mechanism by which the IRS-1 gene variant may lead to development of NIDDM is not known at present. However, compared with glycine, arginine is a much larger molecule and has a polar side chain with a positive charge and a high pKa of 12.5. In IRS-1, codon 972 is located between two YMXM motifs. Although the changes which the glycine for arginine substitution may cause in the tertiary structure of IRS-1 are not known at present, it is assumed that the steric and electrostatic changes of the IRS-1 mutant interfere with the normal interaction between insulin and IGF-1 mediated phosphorylation of neighbouring YMXM motifs of IRS-1 and signal transmitting proteins with src homology 2 domains. Alternatively, the mutation may be a marker associated with another mutation in this or another gene, which other mutation is the one actually involved in disease etiology. This may also be the case with the silent mutations found in the third position of codon 805 (A to G) and in the third position of codon 894 (G to C).

Clinical investigations have shown that NIDDM patients as a whole have insulin resistant glucose disposal to peripheral tissues when compared with glucose-tolerant control subjects. However, glycine$^{972}$-mutation carriers with NIDDM did not differ in their degree of insulin resistance when compared with mutation-negative diabetic patients. Furthermore, the sensitivity of peripheral tissues to insulin was measured in 2 of 3 mutation-positive nondiabetics who turned out to have values of insulin sensitivity within the normal range. In contrast, all mutation carriers had remarkably low fasting plasma concentrations of insulin and C-peptide when compared with matched noncarriers. The combination of comparable insulin sensitivity of peripheral tissues and low basal levels of circulating β-cell secretory products may indicate pancreatic β-cell dysfunction.

In a preferred embodiment, the DNA construct of the invention comprises the DNA sequence shown in the Sequence Listing as SEQ ID NO:1, or a fragment of said DNA sequence including the mutation of G to A at nucleotide 3494 of SEQ ID NO:1.

The length of the DNA construct may vary widely depending on the intended use. For use as an oligonucleotide probe for hybridisation purposes, the DNA fragment may be as short as 17 nucleotides. For expression in a living system as defined above, the DNA construct will typically comprise the full-length DNA sequence encoding IRS-1.

The DNA construct of the invention comprising the mutation in the DNA sequence encoding IRS-1 may suitably be of genomic or cDNA origin, for instance obtained by preparing a genomic or cDNA library and screening for DNA sequences coding for all or part of the IRS-1 by hybridization using synthetic oligonucleotide probes in accordance with standard techniques (cf. Sambrook et al., Molecular Cloning: A Laboratory Manual, 2nd Ed., Cold Spring Harbor, 1989). The probes used should be specific for the mutation. Alternatively, the DNA sequence encoding wild-type IRS-1 may be modified by site-directed mutagenesis using synthetic oligonucleotides containing the mutation for homologous recombination in accordance with well-known procedures. The DNA sequence may also be prepared by polymerase chain reaction using specific primers, for instance as described in U.S. Pat. No. 4,683,202, or Saiki et al., Science 239, 1988, pp. 487-491.

The DNA construct of the invention may also be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed and ligated. This procedure may preferably be used to prepare fragments of the IRS-1 encoding DNA sequence.

The recombinant expression vector into which the DNA construct is inserted may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated (e.g. a viral vector).

In the vector, the mutant DNA sequence encoding IRS-1 should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the mutant DNA encoding IRS-1 in mammalian cells are the SV40 promoter (Subramani et al., Mol. Cell Biol. 1 (1981), 854–864), the MT-1 (metallothionein gene) promoter (Palmiter et al., Science 222 (1983), 809–814) or the adenovirus 2 major late promoter.

The mutant DNA sequence encoding IRS-1 may also be operably connected to a suitable terminator, such as the human growth hormone terminator (Palmiter et al., op. cit.). The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant expression vector may further comprise a DNA sequence enabling the vector to replicate in the host cell in question. An example of such a sequence is the SV40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate.

The procedures used to ligate the DNA sequences coding for IRS-1, the promoter and the terminator, respectively, and to insert them into suitable vectors containing the information necessary for replication, are well known to persons skilled in the art (cf., for instance, Sambrook et al., op.cit.).

In a further aspect, the present invention relates to a variant of IRS-1 containing at least one amino acid substitution, in particular a variant containing at least one amino acid substitution at a site where the substitution interferes with signal transduction through IRS-1, or a fragment thereof including said substitution. An example of such a variant is one in which glycine$^{972}$ is substituted by arginine, or a fragment thereof containing said substitution, e.g. the variant which has the amino acid sequence shown in the Sequence Listing as SEQ ID NO:2, or a fragment thereof containing Arg$^{972}$.

The living system into which the DNA construct of the invention is introduced may be a cell which is capable of producing IRS-1 and which has the appropriate signal transduction pathways. The cell is preferably a eukaryotic cell, such as a vertebrate cell, e.g. a Xenopus laevis oocyte or mammalian cell, in particular a mammalian cell. Examples of suitable mammalian cell lines are the COS (ATCC CRL 1650), BHK (ATCC CRL 1632, ATCC CCL 10), CHL (ATCC CCL39) or CHO (ATCC CCL 61) cell lines. Methods of transfecting mammalian cells and expressing DNA sequences introduced in the cells are described in e.g. Kaufman and Sharp, J. Mol. Biol. 159 (1982), 601–621; Southern and Berg, J. Mol. Appl. Genet. 1 (1982), 327–341; Loyter et al., Proc. Natl. Acad. Sci. USA 79 (1982), 422–426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841–845.

The mutant DNA sequence encoding IRS-1 may then be expressed by culturing a cell as described above in a suitable nutrient medium under conditions which are conducive to the expression of the IRS-1-coding DNA sequence. The medium used to culture the cells may be any conventional medium suitable for growing mammalian cells, such as a serum-containing or serum-free medium containing appropriate supplements. Suitable media are available from commercial suppliers or may be prepared according to published recipes (e.g. in catalogues of the American Type Culture Collection).

The living system according to the invention may also comprise a transgenic animal. A transgenic animal is one in whose genome a heterologous DNA sequence has been introduced. In particular, the transgenic animal is a transgenic non-human mammal, mammals being generally provided with appropriate signal transduction pathways. The mammal may conveniently be a rodent such as a rat or mouse. The mutant DNA sequence encoding IRS-1 may be introduced into the transgenic animal by any one of the methods previously described for this purpose. Briefly, the DNA sequence to be introduced may be injected into a fertilised ovum or cell of an embryo which is subsequently implanted into a female mammal by standard methods, resulting in a transgenic mammal whose germ cells and/or somatic cells contain the mutant DNA sequence. For a more detailed description of a method of producing transgenic mammals, vide B. Hogan et al., *Manipulating the Mouse Embryo*, Cold Spring Harbor Laboratory, Cold Spring Harbor, New York. The mutant DNA sequence may also be introduced into the animal by transfection of fertilised ova with a retrovirus containing the DNA sequence, cf. R. Jaenisch, Proc. Natl. Acad. Sci. USA 73, 1976, pp. 1260–1264. A further method of preparing transgenic animals is described in Gordon and Ruddle, *Methods Enzymol.* 101, 1983, pp. 411–432.

In one embodiment of the present method of detecting the presence of a mutation in the IRS-1 gene, a biological sample is obtained from a subject, DNA (in particular genomic DNA) is isolated from the sample and digested with a restriction endonuclease which cleaves DNA at the site of the mutation, and cleavage of the DNA within the gene encoding IRS-1 at this site is determined. After digestion, the resulting DNA fragments may be subjected to electrophoresis on an agarose gel. DNA from the gel may then be blotted onto a nitrocellulose filter and hybridised with a radiolabelled probe. The probe may conveniently contain a DNA fragment of the IRS-1 gene spanning the mutation (substantially according to the method of E. M. Southern, *J. Mol. Biol.* 98, 1975, pp. 503, e.g. as described by B. J. Conner et al., *Proc. Natl. Acad. Sci. USA* 80, 1983, pp. 278–282).

In a variant of this embodiment, the DNA isolated from the sample may be amplified prior to digestion with the restriction endonuclease. Amplification may suitably be performed by polymerase chain reaction (PCR) using oligonucleotide primers based on the appropriate sequence of IRS-1 spanning the site(s) of mutation, essentially as described by Saiki et al., *Science* 230, 1985, pp. 1350–1354. After amplification, the amplified DNA may be digested with the appropriate restriction endonuclease and subjected to agarose gel electrophoresis. The restriction pattern obtained may be analysed, e.g. by staining with ethidium bromide and visualising bands in the gel by means of UV light. As a control, wild-type DNA encoding IRS-1 (i.e. not containing the mutation) may be subjected to the same procedure, and the restriction patterns may be compared.

In the method of the invention, the sample is preferably analysed for a mutation located at a site where amino acid substitution interferes with signal transduction through IRS-1. A specific example of such a mutation is the mutation of G to A in the first position of codon 972 of the gene encoding IRS-1. This mutation results in a new restriction endonuclease cleavage site 5'-C C A/T G G-3' (SEQ ID NO:3)
3'-G G T/A C C-5' (SEQ ID NO:3) in the mutant DNA sequence coding for IRS-1.

An example of a suitable restriction endonuclease is BstN1.

A further embodiment of the method of the invention is an adaptation of the method described by U. Landegren et al., Science 241, 1988, pp. 1077–1080, which involves the ligation of adjacent oligonucleotides on a complementary target DNA molecule. Ligation will occur at the junction of the two oligonucleotides if the nucleotides are correctly base paired.

In a still further embodiment of the present method, the DNA isolated from the sample may be amplified using oligonucleotide primers corresponding to segments of the gene coding for IRS-1. The amplified DNA may then be analysed by hybridisation with a labelled oligonucleotide probe comprising a DNA sequence corresponding to at least part of the gene encoding IRS-1 and containing a mutation of at least one nucleotide, which mutation corresponds to the mutation the presence of which in the gene encoding IRS-1 is to be detected. As a control, the amplified DNA may furthermore be hybridised with a labelled oligonucleotide probe comprising a DNA sequence corresponding to at least part of the wild-type gene encoding IRS-1. This procedure is, for instance, described by DiLella et al., Lancet 1, 1988, pp. 497–499. Another PCR-based method which may be used in the present invention is the allele-specific PCR method described by R. Saiki et al., Nature 324, 1986, pp. 163–166, or D. Y. Wu et al., Proc. Natl. Acad. Sci. USA 86, 1989, pp. 2757–2760, which uses primers specific for the mutation in the IRS-1 gene.

Other methods of detecting mutations in DNA are reviewed in U. Landegren, GATA 9, 1992, pp. 3–8. A currently preferred method of detecting mutations is by single stranded conformation polymorphism (SSCP) analysis substantially as described by Orita et al., Proc. Natl. Acad. Sci. USA 86, 1989, pp. 2766–2770, or Orita et al., Genomics 5, 1989, pp. 874–879.

The label substance with which the probe is labelled is preferably selected from the group consisting of enzymes, coloured or fluorescent substances, or radioactive isotopes.

Examples of enzymes useful as label substances are peroxidases (such as horseradish peroxidase), phosphatases (such as acid or alkaline phosphatase), β-galactosidase, urease, glucose oxidase, carbonic anhydrase, acetylcholinesterase, glucoamylase, lysozyme, malate dehydrogenase, glucose-6-phosphate dehydrogenase, β-glucosidase, proteases, pyruvate decarboxylase, esterases, luciferase, etc.

Enzymes are not in themselves detectable but must be combined with a substrate to catalyse a reaction the end product of which is detectable. Examples of substrates which may be employed in the method according to the invention include hydrogen peroxide/tetramethylbenzidine or chloronaphthole or o-phenylenediamine or 3-(p-hydroxyphenyl) propionic acid or luminol, indoxyl phosphate, p-nitrophenylphosphate, nitrophenyl galactose, 4-methyl umbelliferyl-D-galactopyranoside, or luciferin.

Alternatively, the label substance may comprise coloured or fluorescent substances, including gold particles, coloured or fluorescent latex particles, dye particles, fluorescein, phycoerythrin or phycocyanin.

In a particularly favoured embodiment, the probe is labelled with a radioactive isotope. Radioactive isotopes which may be used for the present purpose may be selected from I-125, I-131, In-111, H-3, P-32, C-14 or S-35. The radioactivity emitted by these isotopes may be measured in a beta- or gamma-counter or by a scintillation camera in a manner known per se.

For use in the present method, the invention further relates to a test kit for detecting the presence of a mutation in the gene encoding IRS-1, the kit comprising (a) a restriction endonuclease which cleaves DNA at the site of the mutation, (b) a first DNA sequence corresponding to at least part of the wild-type gene encoding IRS-1, and/or (c) a second DNA sequence corresponding to at least part of the gene encoding IRS-1 and containing a mutation of at least one nucleotide, which mutation corresponds to the mutation the presence of which in the gene encoding IRS-1 is to be detected.

The first DNA sequence may, for instance, be obtained from genomic DNA or cDNA encoding IRS-1 obtained from a healthy subject. The second DNA sequence may conveniently be a DNA construct according to the invention.

For use in the present method, the invention further relates to a test kit for detecting the presence of a mutation in the gene encoding IRS-1, the kit comprising (a) means for amplifying DNA, and (b) a labelled oligonucleotide probe comprising a DNA sequence corresponding to at least part of the gene encoding IRS-1 and containing a mutation of at least one nucleotide, which mutation corresponds to the mutation the presence of which in the gene encoding IRS-1 is to be detected.

Appropriate means for amplifying DNA (typically genomic DNA isolated from the biological sample) include, for instance, oligonucleotide primers, appropriate buffers and a thermostable DNA polymerase.

The invention is further illustrated in the following example which is not intended in any way to limit the scope of the invention as claimed.

EXAMPLES

Example 1

Subjects

A total of 86 NIDDM patients and 76 control subjects were included in the protocol. All study participants were unrelated Danish Caucasians and their clinical characteristics are given in Table 1 and 2. The control subjects had normal fasting plasma glucose levels and no family history of known diabetes. Patients with NIDDM, as defined by the National Diabetes Data Group (18), were recruited consecutively and unselected from the outpatient clinic at Steno Diabetes Center. All NIDDM patients were treated with diet, oral hypoglycemic drugs, or both. None of the participants in the study suffered from liver or kidney diseases as evaluated by clinical and standard laboratory examinations, and no subject was taking any other medication known to influence pancreatic β-cell function or energy metabolism. Before participation, the purpose and risks of the study were carefully explained to all volunteers and their informed consent was obtained. The protocol was approved by the local Ethical Committee of Copenhagen and was in accordance with the Helsinki declaration.

Euglycemic, Hyperinsulinemic Clamp

NIDDM patients and 19 glucose-tolerant healthy control subjects were examined using a euglycemic, hyperinsulinemic clamp. The experiments were undertaken in the fasting state between 08.00 and 15.00 after a 10 h overnight fast. Each clamp comprised a 2 h basal period followed by a 4 h hyperinsulinemic glucose clamp. Details of the clamp technique have been described previously (19). To assess total peripheral glucose uptake, (3-$^3$H) glucose was infused throughout the study period. In the control subjects, (3-$^3$H) glucose was administered as a primed (25-$\mu$Ci) continuous (0.25-$\mu$Ci/min) infusion, whereas in the NIDDM subjects, the priming was increased in proportion to the increase in fasting plasma glucose concentration; the continuous infusion of labeled glucose was the same as in the control subjects (0.25 $\mu$Ci/min). The clamp was performed by continuous infusion of 2 mU insulin×kg$^{-1}$×min$^{-1}$ (Actrapid, Novo Nordisk, Denmark), and euglycemia was maintained by a variable infusion of 20% glucose at a rate determined by the measurement of plasma glucose levels at 5 to 10 min invervals. Total glucose disposal rate was calculated from the plasma concentrations of (3-$^3$H) glucose and plasma glucose with Steele's non-steady state equations (20). In these calculations, the distribution volume of glucose was taken as 200 ml/kg body weight and the pool fraction as 0.65. At the highest steady state plasma insulin level, where the hepatic glucose production is presumed to be nil, glucose infusion rates were used to calculate glucose disposal. Total peripheral glucose uptake was corrected for urinary glucose loss.

Preparation and Amplification of Genomic DNA

Genomic DNA was isolated from human leucocyte nuclei isolated from whole blood by protein kinase K digestion followed by phenol extraction on a Applied Biosystems 341 Nucleic Acid Purification System. A primary 50 $\mu$l PCR reaction was carried out with 0,3 $\mu$g of genomic DNA. The assay conditions were: 10 mM Tris-HCl (pH 9.0), 50 mM KCl, 1.5 mM MgCl$_2$, 0.1% Triton X-100, 0.2 mM dNTP's, 0.2 $\mu$M of each oligonucleotide primer and 1.25 u Taq DNA polymerase (Promega, Madison, Wis.). Specific oligonucleotide primers for the human IRS-1 gene (4), 20–25 mers and 2 G's or C's at the 3' end, were synthezised on an Applied Biosystems 394 DNA/RNA syntheziser (Applied Biosystems Inc., Foster City, Calif.) and eluted on a NAB-10 column (Pharmacia P-L Biochemicals Inc, Milwaukee, Wis.) and used without further purification.

The nucleotide sequences of the DNA primers used for the polymerase chain reactions were as follows:

| 1.  | 553  | 5'GCTCAGCGTTGGTGGTGGCGGTGG3'   | 577 (SEQ ID NO: 4)   |
|-----|------|--------------------------------|----------------------|
| 2.  | 783  | 3'CGACGAAGTTGTAGTTGTTCGCCCG5'  | 807 (SEQ ID NO: 5)   |
| 3.  | 727  | 5'GAAGTGGCGGCACAAGTCGAGCGC3'   | 756 (SEQ ID NO: 6)   |
| 4.  | 999  | 3'CGAGGCCGGAACCACTCCGACC5'     | 1020 (SEQ ID NO: 7)  |
| 5.  | 924  | 5'ACCGTGCTAAGGGCCACCACGACG3'   | 947 (SEQ ID NO: 8)   |
| 6.  | 1180 | 3'CCTCCGTCGCCGGCACCACGA5'      | 1200 (SEQ ID NO: 9)  |
| 7.  | 1128 | 5'TCTACCGCCTTTGCCTGACCAGC3'    | 1150 (SEQ ID NO: 10) |
| 8.  | 1392 | 3'CGGTCAGGAGCAGGTTGACG5'       | 1411 (SEQ ID NO: 11) |
| 9.  | 1337 | 5'ACCATCCTGGAGGCCATGCGG3'      | 1357 (SEQ ID NO: 12) |
| 10. | 1598 | 3'GGTCGGAGCCACCTGCCGTCGGGA5'   | 1621 (SEQ ID NO: 13) |
| 11. | 1545 | 5'CAGGCTCCTTCCGTGTCCGCG3'      | 1565 (SEQ ID NO: 14) |
| 12. | 1807 | 3'GGGTGCCGCTAGATCACGAAG5'      | 1827 (SEQ ID NO: 15) |
| 13. | 1757 | 5'CTGTCGTCCAGTAGCACCAGTGG3'    | 1779 (SEQ ID NO: 16) |
| 14. | 2007 | 3'GGGACTGGCGGGGGTTGCCAG5'      | 2037 (SEQ ID NO: 17) |
| 15. | 1953 | 5'GCGGTGAGGAGGAGCTAAGC3'       | 1932 (SEQ ID NO: 18) |
| 16. | 2200 | 3'GGGCAGGGTCAGGAGTCACCG5'      | 2230 (SEQ ID NO: 19) |
| 17. | 2151 | 5'AGAGAACTCACTCGGCAGGC3'       | 2170 (SEQ ID NO: 20) |
| 18. | 2401 | 3'GGTGTGCCTACTACCGATGTACGG5'   | 2424 (SEQ ID NO: 21) |
| 19. | 2352 | 5'ACCCCTTGGAGCGTCGGGGG3'       | 2371 (SEQ ID NO: 22) |
| 20. | 2600 | 3'GGACTGAATCCTCCACCGGGGTCG5'   | 2623 (SEQ ID NO: 23) |
| 21. | 2546 | 5'CAGAGAGTGGACCCCAATGG3'       | 2566 (SEQ ID NO: 24) |
| 22. | 2800 | 3'CCTGAGGTTGTGGTCGTCGG5'       | 2819 (SEQ ID NO: 25) |
| 23. | 2712 | 5'TCTTGCCTCACCCCAAACCC3'       | 3150 (SEQ ID NO: 26) |
| 24. | 2964 | 3'CGAGACCAGCGGAAGAGATA5'       | 2983 (SEQ ID NO: 27) |
| 25. | 2918 | 5'GAGCCGGAGGAGGGTGCCCG3'       | 2938 (SEQ ID NO: 28) |
| 26. | 3180 | 3'GGTTCCGGTCGTGGAATGGA5'       | 3199 (SEQ ID NO: 29) |
| 27. | 3131 | 5'CAGACCAATAGCCGCCTGGC3'       | 3150 (SEQ ID NO: 30) |
| 28. | 3392 | 3'CCGTGACTCCTCATGTACTT5'       | 3411 (SEQ ID NO: 31) |
| 29. | 3339 | 5'CTTCTGTCAGGTGTCCATCC3'       | 3358 (SEQ ID NO: 32) |
| 30. | 3582 | 3'CGATGCACCTGTGGAGCGGT5'       | 3601 (SEQ ID NO: 33) |
| 31. | 3532 | 5'GGGCAGTGCCCAGCAGCCGG3'       | 3541 (SEQ ID NO: 34) |
| 32. | 3743 | 3'CGACGGGTGAGCAGGGACGACC5'     | 3764 (SEQ ID NO: 35) |
| 33. | 3687 | 5'CCTCAGCAGCCTCTGCTTCC3'       | 3712 (SEQ ID NO: 36) |
| 34. | 3950 | 3'CGTCGTCATCCCCCGCCACC5'       | 3969 (SEQ ID NO: 37) |
| 35. | 3900 | 5'CCACACCCAGTGCCACCCGG3'       | 3919 (SEQ ID NO: 38) |
| 36. | 4141 | 3'CCTGAAGTTTGTCACGGGAG5'       | 4160 (SEQ ID NO: 39) |
| 37. | 4067 | 5'GAGCCAGCCAAACTGTGTGG3'       | 4086 (SEQ ID NO: 40) |
| 38. | 4320 | 3'CCTGTAGTGTCGTCCAGCAA5'       | 4339 (SEQ ID NO: 41) |

The mixture was overlaid with 40 $\mu$l of mineral oil and after initial denaturation at 95° C. for 3 min, the samples were subjected to 35 cycles of amplification: annealing at 60° C. for 1 min, extension at 72° C. for 2 min and denaturation at 94° C. for 1 min. In these primary PCR reactions, fragments of 800–900 bp, were amplified. A secondary PCR reaction was performed with 1 $\mu$l of a 1:10 diluted primary PCR product as template. The amplification conditions were as described above, except that ($\alpha$-$^{32}$P) dCTP (Amersham International, Buckinghamshire, UK) was added. Each fragment amplified during secondary PCR had a size of 250–285 bp.

Single Stranded Conformation Polymorphism (SSCP) Analysis

In the primary mutation screening, SSCP analysis (according to the method of Orita et al., *Genomics* 5, 1989, pp. 874–879) of the entire coding region of IRS-1 was performed on genomic DNA from 19 insulin resistant NIDDM patients and 5 control subjects (Table 1). In all cases, 2 µl of a secondary PCR product was combined with 8 µl of a sequencing stop solution. One µl was loaded unheated to identify double-stranded products and after heating at 94° C. for 5 min, 2 µl was loaded to the same wells on a 38×31×0,03 cm 5% polyacrylamid gel (49:1, acrylamid:bisacrylamid) in 90 mM Tris-borate, 2,5 mM EDTA, with 1% or 5% glycerol, respectively. In each patient SSCP analysis was undertaken at 2 different experimental conditions: electrophoresis was carried out with 1% glycerol at 35 W constant power for 4–5 h at 4° C. by placing gel, buffer and electrophoresis apparatus at 4° C. overnight, and with 5% glycerol at 65 W constant power for 2–3 hours at 25° C. (21). The gels were transferred to 3 MM filter paper, covered with a plastic wrap and autoradiographed at –80° C. with intensifying screens for 2–10 h. Gels contained 2 lanes with a known plasmid mutation and the corresponding wild type fragment as positive controls. In our laboratory the ability to detect known plasmid mutations (single base substitutions, small insertions, or small deletions) is 80–90% (22).

Synthesis of Single-Stranded DNA and Direct Nucleotide Sequencing

Single stranded DNA for sequencing was generated using biotinylated oligonucleotide primers and streptavidin-coated magnetic beads (available from Dynal AS, Oslo, Norway). Products were precipitated with ammoniumacetate and isopropanol and resuspended in appropiate volumes of water. Sequencing using the AutoRead Sequencing Kit (Pharmacia, Uppsala, Sweden) and Fluore-dATP was analysed on an automated laser fluorescence DNA sequencer (Pharmacia, Uppsala, Sweden).

Direct Restriction Enzyme Digestion of PCR Products

Restriction enzyme digestion was carried out in 15 µl reactions, containing 10 µl precipitated secondary PCR product, 1,5 µl 10× NE buffer 2, 100 µg/ml bovine serum albumin and 10 u of the restriction enzyme BstN 1 (New England BioLabs Inc., Beverly, Mass.). The fragments were analyzed on a 4.5% high solution agarose gel and visualized after staining with ethidium bromide.

Synthesis of cDNA

Percutaneous muscle biopsies (~500 mg) were obtained under local anesthesia from the vastus lateralis muscle of the thigh. Muscle samples were blotted to remove blood and connective and adipose tissue and were within 30 sec frozen in liquid $N_2$ and stored at –80° C. until assayed. Total RNA was isolated from muscle biopsies as described (23). cDNA was synthesized in 25 µl volumes containing 1 µg of total RNA, 0.2 mM deoxynucleoside triphosphates, 40 u RNasin (Promega, Madison, Wis.), 0.625 µg oligo $(dT)_{18}$, 400 u Moloney Murine Leukaemia Virus Reverse Transcriptase (Life Technologies Inc., Grand Island, N.Y.), 50 mM Tris-HCl (pH 8.3), 75 mM KCl, 3 mM $MgCl_2$ and 10 mM DTT. The reactions were performed at 37° C. for 1 hour, followed by enzyme inactivation by incubation for 10 min at 95° C. SSCP was performed on cDNA as described for genomic DNA.

Other Assays

Plasma for analysis of chemical quantities was drawn from all study participants in the morning after 10 h of overnight fast. Plasma glucose was measured in duplicate by a hexokinase method. Tritiated glucose in plasma was determined as described (24). $HbA_{1C}$ was measured using a HPLC method (normal range 4.1–6.4%). Plasma insulin and C-peptide levels were analyzed by radioimmuno-assays (25,26).

Statistical Analysis

Data in text and tables are given as means±SE. For comparisons Mann-Whitney's test for unpaired data was applied.

Primary Screening for Mutations in the IRS-1 Gene

Figure 2:
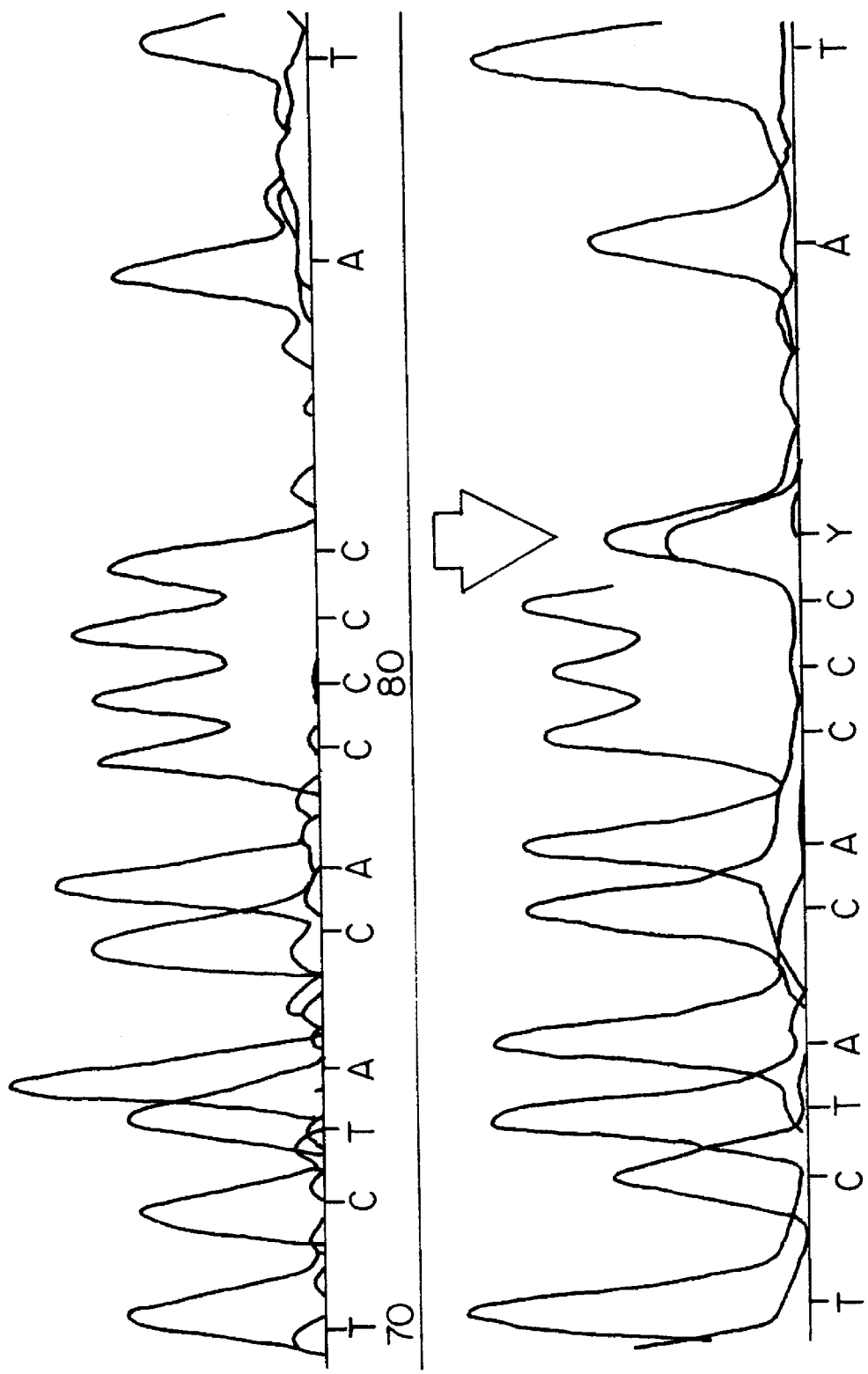
FIG. 2 shows direct nucleotide sequencing of a part of the 3338–3600 base pair fragment of IRS-1. The sequencing was performed on the noncoding strand (c.f. Table 3). Upper panel shows the wild type sequence whereas lower panel depicts the nucleotide sequence from an individual who is heterozygous for a single base substitution in the coding strand at nucleotide position 3494 as indicated by an arrow, (G→A) (c.f. Table 3). The base substitution in codon$^{972}$ caused a substitution of glycine with arginine.

In 19 overlapping fragments, each consisting of 250–285 bp, the entire coding region of the IRS-1 gene was analyzed using genomic DNA from 19 NIDDM patients and 5 control subjects. Compared with matched control subjects the NIDDM patients were as a group hyperinsulinemic ($p<0.02$) and were characterized by impaired insulin stimulated glucose disposal to peripheral tissues ($p<0.0001$) (Table 1). SSCP scanning showed 3 different aberrant migration profiles. Subsequent nucleotide sequencing revealed one polymorphism at codon 805 (GCA→GCG (alanine)). Four of 19 NIDDM patients were heterozygous for this single base substitution which did not predict any change in the amino acid sequence. Another silent mutation was detected at codon 894 (CCG→CCC (proline)). Only one of 19 NIDDM patients was heterozygous for this nucleotide base variation. However, at codon 972 SSCP analysis showed that three of 19 NIDDM patients were heterozygous for a mutation in which glycine (GGG) was substituted for arginine (AGG) (FIGS. 1 and 2). The mutation was confirmed by sequencing of both DNA strands and by direct enzymatic digestion of PCR products with the restriction enzyme Bst N1, for which a restriction site was created by the nucleotide substitution (data not shown). None of the 5 control subjects, who primarily were SSCP scanned, showed evidence of polymorphisms. The glycine 972 mutation was located between 2 Tyr-Met-X-Met motifs in the IRS-1 gene (Table 3). Subsequently, the codon 972 mutation, primarily identified on genomic DNA isolated from blood cells, was verified by studies of cDNA, synthesized from total RNA which was isolated from skeletal muscle biopsies.

Secondary Screening for Glycine$^{972}$ Mutation

Using SSCP molecular scanning and specific enzymatic digestion of primary PCR products further 67 NIDDM patients (Table 2) and 76 healthy control subjects were examined for the occurrence of the glycine$^{972}$ mutation. Seven of the 67 NIDDM patients were heterozygous for the mutation. Moreover, 3 of 76 healthy volunteers were also heterozygous carriers of the codon$^{972}$ mutation. All 3 control subjects who were positive for the mutation had a normal glucose response to an oral glucose challenge (data not shown).

Clinical Characterization of Individuals Carrying the Glycine$^{972}$ Mutation

Table 1 shows the results obtained from the clinical investigations of the 3 glucose-tolerant controls who were positive for the glycine$^{972}$ mutation. Insulin-glucose clamp was performed in 2 of the 3 mutation carriers and the glucose disposal rates of these individuals were within the range of the 19 mutation-negative control subjects. However, interestingly also glucose-tolerant mutation carriers were characterized by relatively low values of fasting plasma insulin (decreased by 33–46%) and C-peptide (decreased by 25–40%), respectively, when compared with mean values obtained in mutation-negative healthy controls.

Table 2 gives a summary of the phenotypical characteristics of the 10 NIDDM patients who are heterozygous carriers of the glycine$^{972}$ mutation in the IRS-1 gene when compared to 76 NIDDM patients who are negative for the same mutation. No significant differences were shown in age, known diabetes duration, body mass index, fasting levels of plasma glucose, $HbA_{1C}$ and basal or insulin stimulated glucose disposal rates. However, fasting plasma levels of insulin and C-peptide were reduced by 44% (p <0.05) and 37% (p<0.02), respectively, in diabetics who were positive for the glycine$^{972}$ mutation when compared with mutation-negative diabetic subjects.

Example 2

A random sample of 383 unrelated healthy young Caucasians (15–32 years of age) was studied to determine whether the glycine$^{972}$ mutation confers insulin resistance. All individuals had their insulin sensitivity estimated using Bergman's minimal model (intravenous injections of glucose combined with tolbutamide), and the occurrence of the glycine$^{972}$ mutation was determined by means of SSCP scanning (as described in Example 1) and restriction enzyme analysis of genomic DNA (as described in Example 1). 35 subjects were found to carry the mutation.

Those carriers of the glycine$^{972}$ mutation who had a body mass index (BMI) of more than 25 kg/m$^2$ (n=10, BMI=28.4±0.9 kg/m$^2$) (mean±standard error) had a two-fold lower insulin sensitivity and a significantly higher fasting serum level of C-peptide than the non-carriers with the same BMI (n=99, BMI=28.1±0.3 kg/m$^2$). In contrast, there was no difference in the measured variables between the carriers and non-carriers of the mutation in subjects with a BMI of less than 25 kg/m$^2$. In multivariate analysis adjusting for differences in VO$_2$ max, BMI, gender and age, the presence of the glycine$^{972}$ mutation within the group of obese subjects was negatively associated with insulin sensitivity (p<0.04) and positively associated with fasting serum C-peptide (p<0.09), fasting serum triglyceride (p<0.02) and serum total cholesterol (p<0.03).

The results of the study show that in young obese subjects, the glycine$^{972}$ mutation is associated with whole-body insulin resistance and dyslipidemia.

REFERENCES

1. Hitman GA, McCarthy MI. Genetics of non-insulin-dependent diabetes mellitus. Baillieres Clin Endocrinol Metab 1991; 5:455–476.
2. DeFronzo RA. The triumverate: β-cell, muscle, liver: a collision responsible for NIDDM. Diabetes 1988; 37:667–687.
3. Kahn CR, White MF. The insulin receptor and the molecular mechanism of insulin action. J Clin Invest 1988; 82:1151–1156.
4. Sun XJ, Rothenberg P, Kahn CR, et al. Structure of the insulin receptor substrate IRS-1 defines a unique signal transduction protein. Nature (Lond ) 1991; 352:73–77.
5. Rothenberg P, Lane WS, Karasik A, Backer J, White MF, Kahn CR. Purification and partial sequence analysis of pp185, the major cellular substrate of the insulin receptor tyrosine kinase. J Biol Chem 1991; 266:8302–8311.
6. Nishiyama M, Wands JR. Cloning and increased expression of an insulin receptor substrate-1-like gene in human hepatocellular carcinoma. Biochem Biophys Res 1992; 183:280–285.
7. Backer JM, Schroeder GG, Kahn CR, et al. Insulin stimulation of phosphatidylinositol 3-kinase activity maps to insulin receptor regions required for endogenous substrate phosphorylation. J Biol Chem 1992; 267:1367–1364.
8. Myers Jr MG, Backer JM, Sun XJ, et al. IRS-1 activates phosphatidylinositol 3-kinase by associating with src homology 2 domains of p85. Proc Natl Acad Sci USA 1992; 89:10350–10354.
9. Backer JM, Myers Jr MG, Shoelson SE, et al. Phosphatidylinositol 3-kinase is activated by association with IRS-1 during insulin stimulation. The EMBO Journal 1992; 11: 3469–3479.
10. Yonezawa K, Ueda H, Hara K, et al. Insulin-dependent formation of a complex containing an 85-kDa subunit of phosphatidylinositol 3-kinase and tyrosine-phosphorylated insulin receptor substrate 1. J Biol Chem 1992; 267:25958–25966.
11. Folli F, Saad MJA, Backer JM, Kahn CR. Insulin stimulation of phosphatidylinositol 3-kinase activity and association with insulin receptor substrate 1 in liver and muscle of the intact rat. J Biol Chem 1992; 267:22171–22177.
12. Yonezawa K, Yokono K, Shii K, et al. In vitro association of phosphatidylinositol 3-kinase activity with the activated insulin receptor tyrosine kinase. J Biol Chem 1992; 267:440–446.
13. Hayashi H, Kamohara S, Nishioka Y, et al. Insulin treatment stimulates the tyrosine phosphorylation of the α-type 85-kDa subunit of phosphatidylinositol 3-kinase in vivo. J Biol Chem 1992; 267:22575–22580.
14. Sun XJ, Miralpeix M, Myers Jr MG, et al. Expression and function of IRS-1 in insulin signal transmission. J Biol Chem 1992; 267:22662–22672.
15. Shoelson SE, Chatterjee S, Chaudhuri M, White MF. YMXM motifs of IRS-1 define substrate specificity of the insulin receptor kinase. Proc Natl Acad Sci USA 1992; 89:2027–2031.
16. McClain DA, Maegawa H, Scott Thies R, Olefsky JM. Dissection of the growth versus metabolic effects of insulin and insulin-like growth factor-I in transfected cells expressing kinase-defective human insulin receptors. J Biol Chem 1990; 265:1678–1682.
17. Taylor SI, Cama A, Accili D. Molecular genetics of insulin resistant diabetes mellitus. J Clin Endocrinol Metab 1991; 73:1158–1163.
18. National Diabetes Data Group . Classification and diagnosis of diabetes mellitus and other categories of glucose intolerance. Diabetes 1979; 28:1039–1057.
19. DeFronzo RA, Tobin JD, Andres R. Glucose clamp technique: a method for quantifying insulin secretion and resistance. Am J Physiol 1979; 237:E214–E223.
20. Steele R. Influence of glucose loading and of injected insulin on hepatic glucose production. Ann NY Acad Sci 1959; 82:420–430.
21. Orita M, Iwahana H, Kanazawa H, Hayashi K, Sekiya T. Detections of polymorphisms of human DNA by gel electrophoresis as single-stranded conformation polymorphisms. Proc Natl Acad Sci USA 1989; 86:2766–2770.
22. Vestergaard H, Bjørbæk C, Andersen PH, Bak JF, Pedersen 0. Impaired expression of glycogen synthase mRNA in skeletal muscle of NIDDM patients. Diabetes 1991; 40:1740–1745.
23. Chomczynski P, Sachhi N. Single-step method of RNA isolation by acid guanidinium thiocyanate-phenol-chloroform extraction. Anal Biochem 1987; 162:156–159.
24. Hother-Nielsen O, Schmitz O, Bak JF, Beck-Nielsen H. Enhanced hepatic insulin sensitivity, but peripheral insulin resistance in patients with type I (insulin-dependent) diabetes. Diabetologia 1987; 30:834–840.
25. Heding LG. Determination of total serum insulin (IRI) in insulin-treated diabetic patients. Diabetologia 1972; 8:260–266.
26. Heding LG. Radioimmunological determination of human C-peptide in serum. Diabetologia 1975; 11:541–548.
27. White MF, Maron R, Kahn CR. Insulin rapidly stimulates tyrosine phosphorylation of a Mr 185,000 protein in intact cells. Nature (Lond ) 1985; 318:183–186.
28. White MF, Stegmann EW, Dull TJ, Ullrich A, Kahn CR. Characterization of an endogenous substrate of the insulin receptor in cultured cells. J Biol Chem 1987; 262:9769–9777.

TABLE 1

Phenotypical characterization of 19 NIDDM patients who were examined with the primary SSCP scanning of the IRS-1 gene: comparisons to 19 matched controls without detected IRS-1 mutations and 3 glucose-tolerant controls in whom glycine$^{972}$ was substituted with arginine

|  | N (F:M) | Age (yr) | Body Mass Index (kg/m$^2$) | HbA$_{1C}$ (%) | Plasma glucose (mM) | Plasma insulin (pM) | Plasma C-peptide (nM) | M-value (basal) | M-value (insulin) |
|---|---|---|---|---|---|---|---|---|---|
| NIDDM | | | | | | | | | |
| Mean | 6/13 | 54 | 29 | 7.9 | 10.4 | 95 | 0.92 | 88 | 330 |
| ±SE | | 2 | 1 | 0.5 | 0.9 | 13 | 0.09 | 3 | 30 |
| CONTROL (noncarriers of mutation) | | | | | | | | | |
| Mean | 7/12 | 50 | 28 | 5.4* | 5.5* | 60+ | 0.67§ | 77+ | 484* |
| ±SE | | 2 | 1 | 0.1 | 0.1 | 6 | 0.04 | 2 | 30 |
| CONTROL (carriers of mutation) | | | | | | | | | |
| No. 1 | F | 50 | 27 | 4.7 | 5.1 | 32 | 0.40 | 71 | 461 |
| No. 2 | M | 64 | 23 | 5.6 | 6.0 | 40 | 0.51 | 78 | 389 |
| No. 3 | M | 66 | 23 | 6.0 | 5.9 | 34 | 0.42 | ND | ND |

Plasma levels of glucose, insulin and C-peptide were measured in the fasting state in the morning. M-value is the glucose disposal rate (mg/m$^2$/min) in the fasting state (basal) in the morning and after 4 hours of euglycemic and hyperinsulinemic clamp (insulin) with steady state plasma insulin concentrations during the last 30 min of the clamp of 1165 ± 71 pM in NIDDM patients and 1034 ± 56 pM in controls who were noncarriers of the glycine$^{972}$ mutation. In the 3 glucose-tolerant mutation carriers the steady state plasma insulin levels were 786 pM (subject no. 1) and 1008 pM (subject no. 2), respectively.
ND = not determined.
*$P < 10^{-4}$ vs. NIDDM;
+$P < 0.02$ vs. NIDDM;
§$P < 0.03$ vs. NIDDM.

TABLE 2

Characteristics of 10 NIDDM patients who are carriers of the glycine$^{972}$ –> arginine mutation in the IRS-1 gene: comparisons to NIDDM patients who are noncarriers of the mutation

|  | +Mutation | –Mutation |
|---|---|---|
| N (F/M) | 3/7 | 30/46 |
| Age (yr) | 52 ± 2 | 54 ± 1 |
| Body Mass Index (kg/m$^2$) | 29 ± 2 | 30 ± 1 |
| Known duration of diabetes (yr) | 5 ± 1 | 4 ± 1 |
| HbA$_{1C}$ (%) | 8.6 ± 0.6 | 8.0 ± 0.2 |
| Plasma glucose (mM) | 12.4 ± 1.1 | 11.7 ± 0.5 |
| Plasma insulin (pM) | 53 ± 10 | 94 ± 8* |
| Plasma C-peptide (nM) | 0.49 ± 0.06 | 0.78 ± 0.05 + |
| M-value (basal) | 86 ± 5 | 91 ± 3 |
| M-value (insulin) | 286 ± 29 | 265 ± 16 |

Value are means ± SE. Plasma concentrations of glucose, insulin and C-peptide were measured in the fasting state in the morning. M-value is the glucose disposal rate (mg/m$^2$/min) in the fasting state (basal) in the morning and after 4 hours of euglycemic and hyperinsulinemic clamp (insulin) with steady state plasma insulin concentrations during the last 30 min of the clamp of 980 ± 57 pM in NIDDM patients who were carriers of the glycine$^{972}$ mutation and 1153 ± 34 pM in NIDDM patients who were noncarriers, respectively.
*$P < 0.05$; +$P < 0.02$.

TABLE 3

Partial nucleotide (3392–3562) and amino acid (938–994) sequence of the published human insulin receptor substrate 1 (IRS-1). The glycine to arginine mutation is located at codon 972 (shown in bold). Two YMXM motifs which are putative recognition sites for insulin signal transmission proteins carrying src homology-2 domains are underlined.

bp3392
coding     5'-GGCACTGAGGAGTACATGAAGATGGACCTGGGGCCGGGCCGGAGGGCAGCCTGGCAG
noncoding  3'-CCGTGACTCCTCATGTACTTCTACCTGGACCCCGGCCCGGCCTCCCGTCGGACCGTC aa938      GlyThrGluGlu<u>TyrMetLysMet</u>AspLeuGlyProGlyArgArgAlaAlaTrpGln

TABLE 3-continued

Partial nucloetide (3392–3562) and amino acid (938–994) sequence of the published human insulin receptor substrate 1 (IRS-1). The glycine to arginine mutation is located at codon 972 (shown in bold). Two YMXM motifs which are putative recognition sites for insulin signal transmission proteins carrying src homology-2 domains are underlined.

```
                                                              A
         GAGAGCACTGGGGTCGAGATGGGCAGACTGGGCCCTGCACCTCCCGGGGCGTGCTAGC
         CTCTCGTGACCCCAGCTCTACCCGTCTGACCCGGGACGTGGAGGGCCCCGACGATCG
                                                              Arg
         GluSerThrGlyValGluMetGlyArgLeuGlyProAlaProProGlyAlaAlaSer
                                                              972

ATTTGCAGGCCTACCCGGGCAGTGCCCAGCAGCCGGGGTGACTACATGACCATGCAG-3'
3562
         TAAACGTCCGGATGGGCCCGTCACGGGTCGTCGGCCCCACTGATGTACTGGTACGTC-5'

IleCysArgProThrArgAlaValProSerSerArgGlyAspTyrMetThrMetGln (SEQ ID NOS: 1 and 2)
994
```

We claim:

1. An isolated DNA sequence comprising the sequence of SEQ ID NO:1 encoding insulin receptor substrate 1 (IRS-1), the DNA sequence containing a mutation of at least one nucleotide selected from the group consisting of a mutation of G to A in the first position of codon 972, a mutation of A to G in the third position of codon 805, and a mutation of G to C in the third position of codon 894, wherein the mutation interferes with signal transduction through IRS-1.

2. The DNA sequence of claim 1, wherein the mutation gives rise to at least one amino acid substitution in the IRS-1 sequence.

3. The DNA sequence of claim 1 comprising a mutation of G to A at nucleotide 3494 of SEQ ID NO:1.

4. A recombinant expression vector comprising the DNA sequence of claim 1.

5. An isolated mammalian cell containing and expressing the DNA sequence of claim 3.

6. An isolated IRS-1 protein containing at least one amino acid substitution wherein glycine is substituted by arginine at position 972 in SEQ ID NO:2 and wherein said substitution interferes with signal transduction through IRS-1.

* * * * *

SEQUENCE LISTING ( 1 ) GENERAL INFORMATION:

( i i i ) NUMBER OF SEQUENCES: 41

( 2 ) INFORMATION FOR SEQ ID NO: 1:

( i ) SEQUENCE CHARACTERISTICS:
        ( A ) LENGTH: 6152 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 581..4309

( x i ) SEQUENCE DESCRIPTION: SEQ ID NO: 1:

```
TGGTATTTGG  GCGGCTGGTG  GCGGCGGGGA  CTGTTGGAGG  GTGGGAGGAG  GCGAAGGAGG        60

AGGGAGAACC  CCGTGCAACG  TTGGGACTTG  GCAACCCGCC  TCCCCCTGCC  CAAGGATATT       120

TAATTTGCCT  CGGGAATCGC  TGCTTCCAGA  GGGGAACTCA  GGAGGGAAGG  GGGCGCGCGC       180

TCCTGGAGGG  GCACCGCAGG  GACCCCCGAC  TGTCGCCTCC  CTGTGCCGGA  CTCCAGCCGG       240

GGCGACGAGA  GATGCATCTT  CGCTCCTTCC  TGGTGGCGGC  GGCGGCTGAG  AGGAGACTTG       300

GCTCTCGGAG  GATCGGGGCT  GCCCTCACCC  CGGACGCACT  GCCTCCCCGC  CGGGCGTGAA       360

GCGCCCGAAA  ACTCCGGTCG  GGCTCTCTCC  TGGGCTCAGC  AGCTGCGTCC  TCCTTCAGCT       420

GCCCCTCCCC  GCGCGGGGGG  CGGCGTGGAT  TTCAGAGTCG  GGGTTTCTGC  TGCCTCCAGC       480

CCTGTTTGCA  TGTGCCGGGC  CGCGGCGAGG  AGCCTCCGCC  CCCCACCCGG  TTGTTTTTCG       540

GAGCCTCCCT  CTGCTCAGCG  TTGGTGGTGG  CGGTGGCAGC  ATG  GCG  AGC  CCT  CCG     595
                                                Met  Ala  Ser  Pro  Pro
                                                 1                    5

GAG  AGC  GAT  GGC  TTC  TCG  GAC  GTG  CGC  AAG  GTG  GGC  TAC  CTG  CGC  AAA     643
Glu  Ser  Asp  Gly  Phe  Ser  Asp  Val  Arg  Lys  Val  Gly  Tyr  Leu  Arg  Lys
                    10                     15                         20

CCC  AAG  AGC  ATG  CAC  AAA  CGC  TTC  TTC  GTA  CTG  CGC  GCG  GCC  AGC  GAG     691
Pro  Lys  Ser  Met  His  Lys  Arg  Phe  Phe  Val  Leu  Arg  Ala  Ala  Ser  Glu
                    25                     30                         35

GCT  GGG  GGC  CCG  GCG  CGC  CTC  GAG  TAC  TAC  GAG  AAC  GAG  AAG  AAG  TGG     739
Ala  Gly  Gly  Pro  Ala  Arg  Leu  Glu  Tyr  Tyr  Glu  Asn  Glu  Lys  Lys  Trp
```

```
                        40                              45                              50
CGG   CAC   AAG   TCG   AGC   GCC   CCC   AAA   CGC   TCG   ATC   CCC   CTT   GAG   AGC   TGC        787
Arg   His   Lys   Ser   Ser   Ala   Pro   Lys   Arg   Ser   Ile   Pro   Leu   Glu   Ser   Cys
      55                      60                      65

TTC   AAC   ATC   AAC   AAG   CGG   GCT   GAC   TCC   AAG   AAC   AAG   CAC   CTG   GTG   GCT        835
Phe   Asn   Ile   Asn   Lys   Arg   Ala   Asp   Ser   Lys   Asn   Lys   His   Leu   Val   Ala
70                            75                      80                                  85

CTC   TAC   ACC   CGG   GAC   GAG   CAC   TTT   GCC   ATC   GCG   GCG   GAC   AGC   GAG   GCC        883
Leu   Tyr   Thr   Arg   Asp   Glu   His   Phe   Ala   Ile   Ala   Ala   Asp   Ser   Glu   Ala
                        90                      95                            100

GAG   CAA   GAC   AGC   TGG   TAC   CAG   GCT   CTC   CTA   CAG   CTG   CAC   AAC   CGT   GCT        931
Glu   Gln   Asp   Ser   Trp   Tyr   Gln   Ala   Leu   Leu   Gln   Leu   His   Asn   Arg   Ala
                  105                           110                     115

AAG   GGC   CAC   CAC   GAC   GGA   GCT   GCG   GCC   CTC   GGG   GCG   GGA   GGT   GGT   GGT        979
Lys   Gly   His   His   Asp   Gly   Ala   Ala   Ala   Leu   Gly   Ala   Gly   Gly   Gly   Gly
            120                           125                           130

GGG   GGC   AGC   TGC   AGC   GGC   AGC   TCC   GGC   CTT   GGT   GAG   GCT   GGG   GAG   GAC       1027
Gly   Gly   Ser   Cys   Ser   Gly   Ser   Ser   Gly   Leu   Gly   Glu   Ala   Gly   Glu   Asp
            135                           140                           145

TTG   AGC   TAC   GGT   GAC   GTG   CCC   CCA   GGA   CCC   GCA   TTC   AAA   GAG   GTC   TGG       1075
Leu   Ser   Tyr   Gly   Asp   Val   Pro   Pro   Gly   Pro   Ala   Phe   Lys   Glu   Val   Trp
150                           155                     160                                 165

CAA   GTG   ATC   CTG   AAG   CCC   AAG   GGC   CTG   GGT   CAG   ACA   AAG   AAC   CTG   ATT       1123
Gln   Val   Ile   Leu   Lys   Pro   Lys   Gly   Leu   Gly   Gln   Thr   Lys   Asn   Leu   Ile
                        170                           175                           180

GGT   ATC   TAC   CGC   CTT   TGC   CTG   ACC   AGC   AAG   ACC   ATC   AGC   TTC   GTG   AAG       1171
Gly   Ile   Tyr   Arg   Leu   Cys   Leu   Thr   Ser   Lys   Thr   Ile   Ser   Phe   Val   Lys
                  185                           190                           195

CTG   AAC   TCG   GAG   GCA   GCG   GCC   GTG   GTG   CTG   CAG   CTG   ATG   AAC   ATC   AGG       1219
Leu   Asn   Ser   Glu   Ala   Ala   Ala   Val   Val   Leu   Gln   Leu   Met   Asn   Ile   Arg
            200                           205                           210

CGC   TGT   GGC   CAC   TCG   GAA   AAC   TTC   TTC   TTC   ATC   GAG   GTG   GGC   CGT   TCT       1267
Arg   Cys   Gly   His   Ser   Glu   Asn   Phe   Phe   Phe   Ile   Glu   Val   Gly   Arg   Ser
      215                           220                           225

GCC   GTG   ACG   GGG   CCC   GGG   GAG   TTC   TGG   ATG   CAG   GTG   GAT   GAC   TCT   GTG       1315
Ala   Val   Thr   Gly   Pro   Gly   Glu   Phe   Trp   Met   Gln   Val   Asp   Asp   Ser   Val
230                           235                           240                           245

GTG   GCC   CAG   AAC   ATG   CAC   GAG   ACC   ATC   CTG   GAG   GCC   ATG   CGG   GCC   ATG       1363
Val   Ala   Gln   Asn   Met   His   Glu   Thr   Ile   Leu   Glu   Ala   Met   Arg   Ala   Met
                        250                           255                           260

AGC   GAT   GAG   TTC   CGC   CCT   CGC   AGC   AAG   AGC   CAG   TCC   TCG   TCC   AAC   TGC       1411
Ser   Asp   Glu   Phe   Arg   Pro   Arg   Ser   Lys   Ser   Gln   Ser   Ser   Ser   Asn   Cys
                        265                           270                           275

TCT   AAC   CCC   ATC   AGC   GTC   CCC   CTG   CGC   CGG   CAC   CAT   CTC   AAC   AAT   CCC       1459
Ser   Asn   Pro   Ile   Ser   Val   Pro   Leu   Arg   Arg   His   His   Leu   Asn   Asn   Pro
            280                           285                           290

CCG   CCC   AGC   CAG   GTG   GGG   CTG   ACC   CGC   CGA   TCA   CGC   ACT   GAG   AGC   ATC       1507
Pro   Pro   Ser   Gln   Val   Gly   Leu   Thr   Arg   Arg   Ser   Arg   Thr   Glu   Ser   Ile
      295                           300                           305

ACC   GCC   ACC   TCC   CCG   GCC   AGC   ATG   GTG   GGC   GGG   AAG   CCA   GGC   TCC   TTC       1555
Thr   Ala   Thr   Ser   Pro   Ala   Ser   Met   Val   Gly   Gly   Lys   Pro   Gly   Ser   Phe
310                           315                           320                           325

CGT   GTC   CGC   GCC   TCC   AGT   GAC   GGC   GAA   GGC   ACC   ATG   TCC   CGC   CCA   GCC       1603
Arg   Val   Arg   Ala   Ser   Ser   Asp   Gly   Glu   Gly   Thr   Met   Ser   Arg   Pro   Ala
                        330                           335                           340

TCG   GTG   GAC   GGC   AGC   CCT   GTG   AGT   CCC   AGC   ACC   AAC   AGA   ACC   CAC   GCC       1651
Ser   Val   Asp   Gly   Ser   Pro   Val   Ser   Pro   Ser   Thr   Asn   Arg   Thr   His   Ala
                  345                           350                           355

CAC   CGG   CAT   CGG   GGC   AGG   GCC   CGG   CTG   CAC   CCC   CGC   TCA   AAC   CAC   AGC       1699
His   Arg   His   Arg   Gly   Arg   Ala   Arg   Leu   His   Pro   Pro   Leu   Asn   His   Ser
```

|     |     |     |     |     | 360 |     |     |     | 365 |     |     |     |     | 370 |     |      |
|-----|-----|-----|-----|-----|-----|-----|-----|-----|-----|-----|-----|-----|-----|-----|-----|------|
| CGC | TCC | ATC | CCC | ATG | CCG | GCT | TCC | CGC | TGC | TCC | CGT | TCG | GCC | ACC | AGC | 1747 |
| Arg | Ser | Ile | Pro | Met | Pro | Ala | Ser | Arg | Cys | Ser | Arg | Ser | Ala | Thr | Ser |      |
|     | 375 |     |     |     |     | 380 |     |     |     |     | 385 |     |     |     |     |      |
| CCG | GTC | AGT | CTG | TCG | TCC | AGT | AGC | ACC | AGT | GGC | CAT | GGC | TCC | ACC | TCG | 1795 |
| Pro | Val | Ser | Leu | Ser | Ser | Ser | Ser | Thr | Ser | Gly | His | Gly | Ser | Thr | Ser |      |
| 390 |     |     |     |     | 395 |     |     |     |     | 400 |     |     |     |     | 405 |      |
| GAT | TGT | CTC | TTC | CCA | CGG | CGA | TCT | AGT | GCT | TCG | GTG | TCT | GGT | TCC | CCC | 1843 |
| Asp | Cys | Leu | Phe | Pro | Arg | Arg | Ser | Ser | Ala | Ser | Val | Ser | Gly | Ser | Pro |      |
|     |     |     |     | 410 |     |     |     |     | 415 |     |     |     |     | 420 |     |      |
| AGC | GAT | GGC | GGT | TTC | ATC | TCC | TCG | GAT | GAG | TAT | GGC | TCC | AGT | CCC | TGC | 1891 |
| Ser | Asp | Gly | Gly | Phe | Ile | Ser | Ser | Asp | Glu | Tyr | Gly | Ser | Ser | Pro | Cys |      |
|     |     |     | 425 |     |     |     |     | 430 |     |     |     |     | 435 |     |     |      |
| GAT | TTC | CGG | AGT | TCC | TTC | CGC | AGT | GTC | ACT | CCG | GAT | TCC | CTG | GGC | CAC | 1939 |
| Asp | Phe | Arg | Ser | Ser | Phe | Arg | Ser | Val | Thr | Pro | Asp | Ser | Leu | Gly | His |      |
|     |     | 440 |     |     |     |     | 445 |     |     |     |     | 450 |     |     |     |      |
| ACC | CCA | CCA | GCC | CGC | GGT | GAG | GAG | GAG | CTA | AGC | AAC | TAT | ATC | TGC | ATG | 1987 |
| Thr | Pro | Pro | Ala | Arg | Gly | Glu | Glu | Glu | Leu | Ser | Asn | Tyr | Ile | Cys | Met |      |
| 455 |     |     |     |     | 460 |     |     |     |     | 465 |     |     |     |     |     |      |
| GGT | GGC | AAG | GGG | CCC | TCC | ACC | CTG | ACC | GCC | CCC | AAC | GGT | CAC | TAC | ATT | 2035 |
| Gly | Gly | Lys | Gly | Pro | Ser | Thr | Leu | Thr | Ala | Pro | Asn | Gly | His | Tyr | Ile |      |
| 470 |     |     |     |     | 475 |     |     |     |     | 480 |     |     |     |     | 485 |      |
| TTG | TCT | CGG | GGT | GGC | AAT | GGC | CAC | CGC | TGC | ACC | CCA | GGA | ACA | GGC | TTG | 2083 |
| Leu | Ser | Arg | Gly | Gly | Asn | Gly | His | Arg | Cys | Thr | Pro | Gly | Thr | Gly | Leu |      |
|     |     |     |     | 490 |     |     |     |     | 495 |     |     |     |     | 500 |     |      |
| GGC | ACG | AGT | CCA | GCC | TTG | GCT | GGG | GAT | GAA | GCA | GCC | AGT | GCT | GCA | GAT | 2131 |
| Gly | Thr | Ser | Pro | Ala | Leu | Ala | Gly | Asp | Glu | Ala | Ala | Ser | Ala | Ala | Asp |      |
|     |     |     | 505 |     |     |     |     | 510 |     |     |     |     | 515 |     |     |      |
| CTG | GAT | AAT | CGG | TTC | CGA | AAG | AGA | ACT | CAC | TCG | GCA | GGC | ACA | TCC | CCT | 2179 |
| Leu | Asp | Asn | Arg | Phe | Arg | Lys | Arg | Thr | His | Ser | Ala | Gly | Thr | Ser | Pro |      |
|     |     | 520 |     |     |     |     | 525 |     |     |     |     | 530 |     |     |     |      |
| ACC | ATT | ACC | CAC | CAG | AAG | ACC | CCG | TCC | CAG | TCC | TCA | GTG | GCT | TCC | ATT | 2227 |
| Thr | Ile | Thr | His | Gln | Lys | Thr | Pro | Ser | Gln | Ser | Ser | Val | Ala | Ser | Ile |      |
|     |     | 535 |     |     |     |     | 540 |     |     |     |     | 545 |     |     |     |      |
| GAG | GAG | TAC | ACA | GAG | ATG | ATG | CCT | GCC | TAC | CCA | CCA | GGA | GGT | GGC | AGT | 2275 |
| Glu | Glu | Tyr | Thr | Glu | Met | Met | Pro | Ala | Tyr | Pro | Pro | Gly | Gly | Gly | Ser |      |
| 550 |     |     |     |     | 555 |     |     |     |     | 560 |     |     |     |     | 565 |      |
| GGA | GGC | CGA | CTG | CCG | GGA | CAC | AGG | CAC | TCC | GCC | TTC | GTG | CCC | ACC | CGC | 2323 |
| Gly | Gly | Arg | Leu | Pro | Gly | His | Arg | His | Ser | Ala | Phe | Val | Pro | Thr | Arg |      |
|     |     |     |     | 570 |     |     |     |     | 575 |     |     |     |     | 580 |     |      |
| TCC | TAC | CCA | GAG | GAG | GGT | CTG | GAA | ATG | CAC | CCC | TTG | GAG | CGT | CGG | GGG | 2371 |
| Ser | Tyr | Pro | Glu | Glu | Gly | Leu | Glu | Met | His | Pro | Leu | Glu | Arg | Arg | Gly |      |
|     |     |     | 585 |     |     |     |     | 590 |     |     |     |     | 595 |     |     |      |
| GGG | CAC | CAC | CGC | CCA | GAC | AGC | TCC | ACC | CTC | CAC | ACG | GAT | GAT | GGC | TAC | 2419 |
| Gly | His | His | Arg | Pro | Asp | Ser | Ser | Thr | Leu | His | Thr | Asp | Asp | Gly | Tyr |      |
|     |     | 600 |     |     |     |     | 605 |     |     |     |     | 610 |     |     |     |      |
| ATG | CCC | ATG | TCC | CCA | GGG | GTG | GCC | CCA | GTG | CCC | AGT | GGC | CGA | AAG | GGC | 2467 |
| Met | Pro | Met | Ser | Pro | Gly | Val | Ala | Pro | Val | Pro | Ser | Gly | Arg | Lys | Gly |      |
|     | 615 |     |     |     |     | 620 |     |     |     |     | 625 |     |     |     |     |      |
| AGT | GGA | GAC | TAT | ATG | CCC | ATG | AGC | CCC | AAG | AGC | GTA | TCT | GCC | CCA | CAG | 2515 |
| Ser | Gly | Asp | Tyr | Met | Pro | Met | Ser | Pro | Lys | Ser | Val | Ser | Ala | Pro | Gln |      |
| 630 |     |     |     |     | 635 |     |     |     |     | 640 |     |     |     |     | 645 |      |
| CAG | ATC | ATC | AAT | CCC | ATC | AGA | CGC | CAT | CCC | CAG | AGA | GTG | GAC | CCC | AAT | 2563 |
| Gln | Ile | Ile | Asn | Pro | Ile | Arg | Arg | His | Pro | Gln | Arg | Val | Asp | Pro | Asn |      |
|     |     |     |     | 650 |     |     |     |     | 655 |     |     |     |     | 660 |     |      |
| GGC | TAC | ATG | ATG | ATG | TCC | CCC | AGC | GGT | GGC | TGC | TCT | CCT | GAC | ATT | GGA | 2611 |
| Gly | Tyr | Met | Met | Met | Ser | Pro | Ser | Gly | Gly | Cys | Ser | Pro | Asp | Ile | Gly |      |
|     |     |     | 665 |     |     |     |     | 670 |     |     |     |     | 675 |     |     |      |
| GGT | GGC | CCC | AGC | AGC | AGC | AGC | AGC | AGC | AAC | GCC | GTC | CCT | TCC | GGG | | 2659 |
| Gly | Gly | Pro | Ser | Ser | Ser | Ser | Ser | Ser | Asn | Ala | Val | Pro | Ser | Gly | |      |

|     |     |     |     |     | 680 |     |     |     |     | 685 |     |     |     |     | 690 |     |      |
|-----|-----|-----|-----|-----|-----|-----|-----|-----|-----|-----|-----|-----|-----|-----|-----|-----|------|
| ACC | AGC | TAT | GGA | AAG | CTG | TGG | ACA | AAC | GGG | GTA | GGG | GGC | CAC | CAC | TCT |     | 2707 |
| Thr | Ser | Tyr | Gly | Lys | Leu | Trp | Thr | Asn | Gly | Val | Gly | Gly | His | His | Ser |     |      |
|     | 695 |     |     |     |     | 700 |     |     |     |     | 705 |     |     |     |     |     |      |

| CAT | GTC | TTG | CCT | CAC | CCC | AAA | CCC | CCA | GTG | GAG | AGC | AGC | GGT | GGT | AAG | 2755 |
|-----|-----|-----|-----|-----|-----|-----|-----|-----|-----|-----|-----|-----|-----|-----|-----|------|
| His | Val | Leu | Pro | His | Pro | Lys | Pro | Pro | Val | Glu | Ser | Ser | Gly | Gly | Lys |      |
| 710 |     |     |     |     | 715 |     |     |     |     | 720 |     |     |     |     | 725 |      |

| CTC | TTA | CCT | TGC | ACA | GGT | GAC | TAC | ATG | AAC | ATG | TCA | CCA | GTG | GGG | GAC | 2803 |
|-----|-----|-----|-----|-----|-----|-----|-----|-----|-----|-----|-----|-----|-----|-----|-----|------|
| Leu | Leu | Pro | Cys | Thr | Gly | Asp | Tyr | Met | Asn | Met | Ser | Pro | Val | Gly | Asp |      |
|     |     |     |     | 730 |     |     |     |     | 735 |     |     |     |     | 740 |     |      |

| TCC | AAC | ACC | AGC | AGC | CCC | TCC | GAC | TGC | TAC | TAC | GGC | CCT | GAG | GAC | CCC | 2851 |
|-----|-----|-----|-----|-----|-----|-----|-----|-----|-----|-----|-----|-----|-----|-----|-----|------|
| Ser | Asn | Thr | Ser | Ser | Pro | Ser | Asp | Cys | Tyr | Tyr | Gly | Pro | Glu | Asp | Pro |      |
|     |     |     | 745 |     |     |     |     | 750 |     |     |     |     | 755 |     |     |      |

| CAG | CAC | AAG | CCA | GTC | CTC | TCC | TAC | TAC | TCA | TTG | CCA | AGA | TCC | TTT | AAG | 2899 |
|-----|-----|-----|-----|-----|-----|-----|-----|-----|-----|-----|-----|-----|-----|-----|-----|------|
| Gln | His | Lys | Pro | Val | Leu | Ser | Tyr | Tyr | Ser | Leu | Pro | Arg | Ser | Phe | Lys |      |
|     |     | 760 |     |     |     |     | 765 |     |     |     |     | 770 |     |     |     |      |

| CAC | ACC | CAG | CGC | CCC | GGG | GAG | CCG | GAG | GAG | GGT | GCC | CGG | CAT | CAG | CAC | 2947 |
|-----|-----|-----|-----|-----|-----|-----|-----|-----|-----|-----|-----|-----|-----|-----|-----|------|
| His | Thr | Gln | Arg | Pro | Gly | Glu | Pro | Glu | Glu | Gly | Ala | Arg | His | Gln | His |      |
| 775 |     |     |     |     | 780 |     |     |     |     | 785 |     |     |     |     |     |      |

| CTC | CGC | CTT | TCC | ACT | AGC | TCT | GGT | GGC | CTT | CTC | TAT | GCT | GCA | ACA | GCA | 2995 |
|-----|-----|-----|-----|-----|-----|-----|-----|-----|-----|-----|-----|-----|-----|-----|-----|------|
| Leu | Arg | Leu | Ser | Thr | Ser | Ser | Gly | Gly | Leu | Leu | Tyr | Ala | Ala | Thr | Ala |      |
| 790 |     |     |     |     | 795 |     |     |     |     | 800 |     |     |     |     | 805 |      |

| GAT | GAT | TCT | TCC | TCT | TCC | ACC | AGC | AGC | GAC | AGC | CTG | GGT | GGG | GGA | TAC | 3043 |
|-----|-----|-----|-----|-----|-----|-----|-----|-----|-----|-----|-----|-----|-----|-----|-----|------|
| Asp | Asp | Ser | Ser | Ser | Ser | Thr | Ser | Ser | Asp | Ser | Leu | Gly | Gly | Gly | Tyr |      |
|     |     |     |     | 810 |     |     |     |     | 815 |     |     |     |     | 820 |     |      |

| TGC | GGG | GCT | AGG | CTG | GAG | CCC | AGC | CTT | CCA | CAT | CCC | CAC | CAT | CAG | GTT | 3091 |
|-----|-----|-----|-----|-----|-----|-----|-----|-----|-----|-----|-----|-----|-----|-----|-----|------|
| Cys | Gly | Ala | Arg | Leu | Glu | Pro | Ser | Leu | Pro | His | Pro | His | His | Gln | Val |      |
|     |     |     | 825 |     |     |     |     | 830 |     |     |     |     | 835 |     |     |      |

| CTG | CAG | CCC | CAT | CTG | CCT | CGA | AAG | GTG | GAC | ACA | GCT | GCT | CAG | ACC | AAT | 3139 |
|-----|-----|-----|-----|-----|-----|-----|-----|-----|-----|-----|-----|-----|-----|-----|-----|------|
| Leu | Gln | Pro | His | Leu | Pro | Arg | Lys | Val | Asp | Thr | Ala | Ala | Gln | Thr | Asn |      |
|     |     | 840 |     |     |     |     | 845 |     |     |     |     | 850 |     |     |     |      |

| AGC | CGC | CTG | GCC | CGG | CCC | ACG | AGG | CTG | TCC | CTG | GGG | GAT | CCC | AAG | GCC | 3187 |
|-----|-----|-----|-----|-----|-----|-----|-----|-----|-----|-----|-----|-----|-----|-----|-----|------|
| Ser | Arg | Leu | Ala | Arg | Pro | Thr | Arg | Leu | Ser | Leu | Gly | Asp | Pro | Lys | Ala |      |
|     | 855 |     |     |     |     | 860 |     |     |     |     | 865 |     |     |     |     |      |

| AGC | ACC | TTA | CCT | CGG | GCC | CGA | GAG | CAG | CAG | CAG | CAG | CAG | CAG | CCC | TTG | 3235 |
|-----|-----|-----|-----|-----|-----|-----|-----|-----|-----|-----|-----|-----|-----|-----|-----|------|
| Ser | Thr | Leu | Pro | Arg | Ala | Arg | Glu | Gln | Gln | Gln | Gln | Gln | Gln | Pro | Leu |      |
| 870 |     |     |     |     | 875 |     |     |     |     | 880 |     |     |     |     | 885 |      |

| CTG | CAC | CCT | CCA | GAG | CCC | AAG | AGC | CCG | GGG | GAA | TAT | GTC | AAT | ATT | GAA | 3283 |
|-----|-----|-----|-----|-----|-----|-----|-----|-----|-----|-----|-----|-----|-----|-----|-----|------|
| Leu | His | Pro | Pro | Glu | Pro | Lys | Ser | Pro | Gly | Glu | Tyr | Val | Asn | Ile | Glu |      |
|     |     |     |     | 890 |     |     |     |     | 895 |     |     |     |     | 900 |     |      |

| TTT | GGG | AGT | GAT | CAG | TCT | GGC | TAC | TTG | TCT | GGC | CCG | GTG | GCT | TTC | CAC | 3331 |
|-----|-----|-----|-----|-----|-----|-----|-----|-----|-----|-----|-----|-----|-----|-----|-----|------|
| Phe | Gly | Ser | Asp | Gln | Ser | Gly | Tyr | Leu | Ser | Gly | Pro | Val | Ala | Phe | His |      |
|     |     |     | 905 |     |     |     |     | 910 |     |     |     |     | 915 |     |     |      |

| AGC | TCA | CCT | TCT | GTC | AGG | TGT | CCA | TCC | CAG | CTC | CAG | CCA | GCT | CCC | AGA | 3379 |
|-----|-----|-----|-----|-----|-----|-----|-----|-----|-----|-----|-----|-----|-----|-----|-----|------|
| Ser | Ser | Pro | Ser | Val | Arg | Cys | Pro | Ser | Gln | Leu | Gln | Pro | Ala | Pro | Arg |      |
|     |     | 920 |     |     |     |     | 925 |     |     |     |     | 930 |     |     |     |      |

| GAG | GAA | GAG | ACT | GGC | ACT | GAG | GAG | TAC | ATG | AAG | ATG | GAC | CTG | GGG | CCG | 3427 |
|-----|-----|-----|-----|-----|-----|-----|-----|-----|-----|-----|-----|-----|-----|-----|-----|------|
| Glu | Glu | Glu | Thr | Gly | Thr | Glu | Glu | Tyr | Met | Lys | Met | Asp | Leu | Gly | Pro |      |
| 935 |     |     |     |     | 940 |     |     |     |     | 945 |     |     |     |     |     |      |

| GGC | CGG | AGG | GCA | GCC | TGG | CAG | GAG | AGC | ACT | GGG | GTC | GAG | ATG | GGC | AGA | 3475 |
|-----|-----|-----|-----|-----|-----|-----|-----|-----|-----|-----|-----|-----|-----|-----|-----|------|
| Gly | Arg | Arg | Ala | Ala | Trp | Gln | Glu | Ser | Thr | Gly | Val | Glu | Met | Gly | Arg |      |
| 950 |     |     |     |     | 955 |     |     |     |     | 960 |     |     |     |     | 965 |      |

| CTG | GGC | CCT | GCA | CCT | CCC | AGG | GCT | GCT | AGC | ATT | TGC | AGG | CCT | ACC | CGG | 3523 |
|-----|-----|-----|-----|-----|-----|-----|-----|-----|-----|-----|-----|-----|-----|-----|-----|------|
| Leu | Gly | Pro | Ala | Pro | Pro | Arg | Ala | Ala | Ser | Ile | Cys | Arg | Pro | Thr | Arg |      |
|     |     |     |     | 970 |     |     |     |     | 975 |     |     |     |     | 980 |     |      |

| GCA | GTG | CCC | AGC | AGC | CGG | GGT | GAC | TAC | ATG | ACC | ATG | CAG | ATG | AGT | TGT | 3571 |
|-----|-----|-----|-----|-----|-----|-----|-----|-----|-----|-----|-----|-----|-----|-----|-----|------|
| Ala | Val | Pro | Ser | Ser | Arg | Gly | Asp | Tyr | Met | Thr | Met | Gln | Met | Ser | Cys |      |
|     |     |     | 985 |     |     |     |     | 990 |     |     |     |     | 995 |     |     |      |

| CCC | CGT | CAG | AGC | TAC | GTG | GAC | ACC | TCG | CCA | GCT | GCC | CCT | GTA | AGC | TAT | 3619 |
|-----|-----|-----|-----|-----|-----|-----|-----|-----|-----|-----|-----|-----|-----|-----|-----|------|
| Pro | Arg | Gln | Ser | Tyr | Val | Asp | Thr | Ser | Pro | Ala | Ala | Pro | Val | Ser | Tyr |      |

```
         1000                      1005                      1010
GCT  GAC  ATG  CGA  ACA  GGC  ATT  GCT  GCA  GAG  GAG  GTG  AGC  CTG  CCC  AGG    3667
Ala  Asp  Met  Arg  Thr  Gly  Ile  Ala  Ala  Glu  Glu  Val  Ser  Leu  Pro  Arg
     1015                    1020                     1025

GCC  ACC  ATG  GCT  GCT  GCC  TCC  TCA  TCC  TCA  GCA  GCC  TCT  GCT  TCC  CCG    3715
Ala  Thr  Met  Ala  Ala  Ala  Ser  Ser  Ser  Ser  Ala  Ala  Ser  Ala  Ser  Pro
1030                    1035                     1040                     1045

ACT  GGG  CCT  CAA  GGG  GCA  GCA  GAG  CTG  GCT  GCC  CAC  TCG  TCC  CTG  CTG    3763
Thr  Gly  Pro  Gln  Gly  Ala  Ala  Glu  Leu  Ala  Ala  His  Ser  Ser  Leu  Leu
                         1050                    1055                     1060

GGG  GGC  CCA  CAA  GGA  CCT  GGG  GGC  ATG  AGC  GCC  TTC  ACC  CGG  GTG  AAC    3811
Gly  Gly  Pro  Gln  Gly  Pro  Gly  Gly  Met  Ser  Ala  Phe  Thr  Arg  Val  Asn
                    1065                     1070                    1075

CTC  AGT  CCT  AAC  CGC  AAC  CAG  AGT  GCC  AAA  GTG  ATC  CGT  GCA  GAC  CCA    3859
Leu  Ser  Pro  Asn  Arg  Asn  Gln  Ser  Ala  Lys  Val  Ile  Arg  Ala  Asp  Pro
               1080                     1085                    1090

CAA  GGG  TGC  CGG  CGG  AGG  CAT  AGC  TCC  GAG  ACT  TTC  TCC  TCA  ACA  CCC    3907
Gln  Gly  Cys  Arg  Arg  Arg  His  Ser  Ser  Glu  Thr  Phe  Ser  Ser  Thr  Pro
1095                     1100                    1105

AGT  GCC  ACC  CGG  GTG  GGC  AAC  ACA  GTG  CCC  TTT  GGA  GCG  GGG  GCA  GCA    3955
Ser  Ala  Thr  Arg  Val  Gly  Asn  Thr  Val  Pro  Phe  Gly  Ala  Gly  Ala  Ala
1110                     1115                    1120                     1125

GTA  GGG  GGC  GGT  GGC  GGT  AGC  AGC  AGC  AGC  AGC  GAG  GAT  GTG  AAA  CGC    4003
Val  Gly  Gly  Gly  Gly  Gly  Ser  Ser  Ser  Ser  Ser  Glu  Asp  Val  Lys  Arg
                         1130                    1135                    1140

CAC  AGC  TCT  GCT  TCC  TTT  GAG  AAT  GTG  TGG  CTG  AGG  CCT  GGG  GAG  CTT    4051
His  Ser  Ser  Ala  Ser  Phe  Glu  Asn  Val  Trp  Leu  Arg  Pro  Gly  Glu  Leu
                    1145                    1150                     1155

GGG  GGA  GCC  CCC  AAG  GAG  CCA  GCC  AAA  CTG  TGT  GGG  GCT  GCT  GGG  GGT    4099
Gly  Gly  Ala  Pro  Lys  Glu  Pro  Ala  Lys  Leu  Cys  Gly  Ala  Ala  Gly  Gly
               1160                     1165                    1170

TTG  GAG  AAT  GGT  CTT  AAC  TAC  ATA  GAC  CTG  GAT  TTG  GTC  AAG  GAC  TTC    4147
Leu  Glu  Asn  Gly  Leu  Asn  Tyr  Ile  Asp  Leu  Asp  Leu  Val  Lys  Asp  Phe
          1175                     1180                    1185

AAA  CAG  TGC  CCT  CAG  GAG  TGC  ACC  CCT  GAA  CCG  CAG  CCT  CCC  CCA  CCC    4195
Lys  Gln  Cys  Pro  Gln  Glu  Cys  Thr  Pro  Glu  Pro  Gln  Pro  Pro  Pro  Pro
1190                     1195                    1200                     1205

CCA  CCC  CCT  CAT  CAA  CCC  CTG  GGC  AGC  GGT  GAG  AGC  AGC  TCC  ACC  CGC    4243
Pro  Pro  Pro  His  Gln  Pro  Leu  Gly  Ser  Gly  Glu  Ser  Ser  Ser  Thr  Arg
               1210                     1215                    1220

CGC  TCA  AGT  GAG  GAT  TTA  AGC  GCC  TAT  GCC  AGC  ATC  AGT  TTC  CAG  AAG    4291
Arg  Ser  Ser  Glu  Asp  Leu  Ser  Ala  Tyr  Ala  Ser  Ile  Ser  Phe  Gln  Lys
                    1225                    1230                     1235

CAG  CCA  GAG  GAC  CGT  CAG  TAGCTCAACT  GGACATCACA  GCAGGTCGTT                 4339
Gln  Pro  Glu  Asp  Arg  Gln
               1240

TCATGGTGAC  AAAGTCAGAA  GACAAAACTG  CTTTTAACCT  TGTCCTTGAA  TTCTGTTCTT           4399

CGCCTCTGCC  CCTTCCTGTT  CTTTCCCACT  GCTTCCTCAG  GGAGAATGCA  CTTACATTCT           4459

CAGGGCATAC  AAGATGCTCA  CCCACACTGA  CATTGGCAGA  GAGTCAAACA  AACATGTAGG           4519

AGCAGCCACA  GGAGGGCTTT  TTCGTTTGAG  GAATTCCCAA  GTGAAGTAGT  TACTGCAGTA           4579

TTTTTAAACA  TATATCCTAT  GCCAGTTCTG  CGTTTTGTAG  AGTTCCTCCG  TAAGAAGCTT           4639

GATTTGTTTG  TTGAAGTTTT  CTTTTCACTA  TATATTTAGG  TCAGCCCCTG  GAAGGACAGT           4699

TCTACAAAAA  ATACCCGTTA  ACACAGGGGC  TAAACCCTTC  CTTATCTTAA  ACTATCTTAA           4759

TAGTTTCTGG  GAGCCCTTAA  GGGTGATCTT  ATCAAGTTGT  TCTCTGTACT  TTTGTTCTGT           4819

GATTTCATAA  TACTAGGGCA  ACATAAACAG  CAGCGGGAAG  CATTGATTTC  TATTCATCCT           4879
```

-continued

| | | | | | |
|---|---|---|---|---|---|
| GCCCTAAAAA | GATCAGGAGT | AAGAGCTTTT | TAGAAATATG | TATTTAGAGA | GAAGTACCTA | 4939
| TCTATTTTGT | GATCTCTCAA | GAAAGTAATT | ATGGGTGACG | TTCTCCTTTT | GTTCATGTAC | 4999
| CAGGATTTGT | GAAATATTAT | TCACACAACC | GACCCACCAT | CCCACGGGCC | TGGCCTCTCT | 5059
| TGTACAGGAT | ATGCAGGAAA | CTCTGTATGT | GTCTGGGACC | CATTATTAAG | AGTTATGGGA | 5119
| GTTCATCCTA | GGATGTCTGC | CTTATAGTTA | TCTCTTCTTC | TTGCACTGAG | ACATTACAGA | 5179
| TATCATTTGG | GGGCTACTAT | ATATCTTCTG | TAAAATTACT | TTTATTTGTT | GAAGAAGAAT | 5239
| GCATACTAAG | TCAGGAACAT | GCCTTAATTT | GTTTTGTTTT | GCAATTGAGT | AGAAGGGCTA | 5299
| AACTGTATCC | CTCCACTTTT | AGGGTTATTT | GCCTGTGTGC | CTTTAAGTTC | AAAAGTAGAC | 5359
| ACCACAGTAA | ATGCTGAAAG | TTGGCTTTAG | GTCTTCTGTG | GCTAATGCCG | TATTAAAAAT | 5419
| GAAAACATT | TGTGGTAGAA | ATTAGCCTGC | CCTTCGTTCT | GTTGATCCTG | TTTTCTGGTG | 5479
| GTCATAATTG | TGGGTAGAAG | AGAGTACAGT | TTGCAAATAA | TGTGATGAGT | TGGCAATGCA | 5539
| GAAGTTTCCA | GCATTTGGAA | ACACTTTACT | CTGACAAACT | GATTATCTTG | TGAATTTTAT | 5599
| CTATGCTCCA | CAGAATGAGC | TTTTAAAAGC | ACTGATTTTT | CTTAATTTGT | GTCCATTCAT | 5659
| AAGAAATTAA | TCTGTGCCCT | GGTTTCCTAT | TGACAGGTAT | TTATTTATCA | TGTGTTCATA | 5719
| GTCTTCTTAA | TTCTGTTTCC | AATATTTGAT | CCATATAATT | CTCTATTTTA | TAAAGCAAGA | 5779
| AAAAGGTATA | TGAACACTCA | AATGAAGATT | TTGGGTGATA | TGTTACAAAA | AGCATTTATT | 5839
| TGATCAGTAT | TTACTTCAAC | ATTTATTTTC | ATCATTCACT | AGAAGAAAGA | TTTAATTGTG | 5899
| TATATCAACA | TCAGTAGTAC | AAATCTTGTT | ATATCAAATG | ATGTTTTGG | GAGTTCAGAA | 5959
| TCCCTCAACA | CTTTAAGCAT | TTGTATTATA | AAGTGCCTCA | TTGGTAAAAT | AATGAGAATT | 6019
| TGAAGAAAAC | CAGCCCAGCA | GAACTAAAAT | TTTGGTTTTA | AAGGAGATAA | AGAGAATAAG | 6079
| TTTTTCTTAC | TTGTCATCTT | AATTTGTTTA | GGTTTCTTTT | TATAGAGTAG | AATAAATGAT | 6139
| GTTTGCTCTG | AAG | | | | | 6152

(2) INFORMATION FOR SEQ ID NO: 2:

(i) SEQUENCE CHARACTERISTICS:
        (A) LENGTH: 1243 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Ser Pro Pro Glu Ser Asp Gly Phe Ser Asp Val Arg Lys Val
 1               5                  10                  15

Gly Tyr Leu Arg Lys Pro Lys Ser Met His Lys Arg Phe Val Leu
            20                  25                  30

Arg Ala Ala Ser Glu Ala Gly Gly Pro Ala Arg Leu Glu Tyr Tyr Glu
            35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
            115                 120                 125
```

```
Ala  Gly  Gly  Gly  Gly  Gly  Gly  Ser  Cys  Ser  Gly  Ser  Ser  Gly  Leu  Gly
     130                      135                     140

Glu  Ala  Gly  Glu  Asp  Leu  Ser  Tyr  Gly  Asp  Val  Pro  Pro  Gly  Pro  Ala
145                      150                     155                      160

Phe  Lys  Glu  Val  Trp  Gln  Val  Ile  Leu  Lys  Pro  Lys  Gly  Leu  Gly  Gln
                    165                     170                      175

Thr  Lys  Asn  Leu  Ile  Gly  Ile  Tyr  Arg  Leu  Cys  Leu  Thr  Ser  Lys  Thr
               180                      185                     190

Ile  Ser  Phe  Val  Lys  Leu  Asn  Ser  Glu  Ala  Ala  Val  Val  Leu  Gln
          195                     200                     205

Leu  Met  Asn  Ile  Arg  Arg  Cys  Gly  His  Ser  Glu  Asn  Phe  Phe  Phe  Ile
     210                     215                     220

Glu  Val  Gly  Arg  Ser  Ala  Val  Thr  Gly  Pro  Gly  Glu  Phe  Trp  Met  Gln
225                      230                     235                      240

Val  Asp  Asp  Ser  Val  Val  Ala  Gln  Asn  Met  His  Glu  Thr  Ile  Leu  Glu
               245                     250                     255

Ala  Met  Arg  Ala  Met  Ser  Asp  Glu  Phe  Arg  Pro  Arg  Ser  Lys  Ser  Gln
               260                     265                     270

Ser  Ser  Ser  Asn  Cys  Ser  Asn  Pro  Ile  Ser  Val  Pro  Leu  Arg  Arg  His
          275                     280                     285

His  Leu  Asn  Asn  Pro  Pro  Pro  Ser  Gln  Val  Gly  Leu  Thr  Arg  Arg  Ser
     290                     295                     300

Arg  Thr  Glu  Ser  Ile  Thr  Ala  Thr  Ser  Pro  Ala  Ser  Met  Val  Gly  Gly
305                      310                     315                      320

Lys  Pro  Gly  Ser  Phe  Arg  Val  Arg  Ala  Ser  Ser  Asp  Gly  Glu  Gly  Thr
                    325                     330                      335

Met  Ser  Arg  Pro  Ala  Ser  Val  Asp  Gly  Ser  Pro  Val  Ser  Pro  Ser  Thr
               340                     345                     350

Asn  Arg  Thr  His  Ala  His  Arg  His  Arg  Gly  Arg  Ala  Arg  Leu  His  Pro
          355                     360                     365

Pro  Leu  Asn  His  Ser  Arg  Ser  Ile  Pro  Met  Pro  Ala  Ser  Arg  Cys  Ser
     370                     375                     380

Arg  Ser  Ala  Thr  Ser  Pro  Val  Ser  Leu  Ser  Ser  Ser  Thr  Ser  Gly
385                      390                     395                      400

His  Gly  Ser  Thr  Ser  Asp  Cys  Leu  Phe  Pro  Arg  Arg  Ser  Ser  Ala  Ser
                    405                     410                      415

Val  Ser  Gly  Ser  Pro  Ser  Asp  Gly  Gly  Phe  Ile  Ser  Ser  Asp  Glu  Tyr
               420                     425                     430

Gly  Ser  Ser  Pro  Cys  Asp  Phe  Arg  Ser  Ser  Phe  Arg  Ser  Val  Thr  Pro
          435                     440                     445

Asp  Ser  Leu  Gly  His  Thr  Pro  Pro  Ala  Arg  Gly  Glu  Glu  Glu  Leu  Ser
     450                     455                     460

Asn  Tyr  Ile  Cys  Met  Gly  Gly  Lys  Gly  Pro  Ser  Thr  Leu  Thr  Ala  Pro
465                      470                     475                      480

Asn  Gly  His  Tyr  Ile  Leu  Ser  Arg  Gly  Gly  Asn  Gly  His  Arg  Cys  Thr
                    485                     490                      495

Pro  Gly  Thr  Gly  Leu  Gly  Thr  Ser  Pro  Ala  Leu  Ala  Gly  Asp  Glu  Ala
               500                     505                     510

Ala  Ser  Ala  Ala  Asp  Leu  Asp  Asn  Arg  Phe  Arg  Lys  Arg  Thr  His  Ser
          515                     520                     525

Ala  Gly  Thr  Ser  Pro  Thr  Ile  Thr  His  Gln  Lys  Thr  Pro  Ser  Gln  Ser
     530                     535                     540

Ser  Val  Ala  Ser  Ile  Glu  Glu  Tyr  Thr  Glu  Met  Met  Pro  Ala  Tyr  Pro
545                      550                     555                      560
```

| | | | | | | | | | | | | | |
|---|---|---|---|---|---|---|---|---|---|---|---|---|---|
| Pro | Gly | Gly | Gly | Ser | Gly | Gly | Arg | Leu | Pro | Gly | His | Arg | His | Ser | Ala |
| | | | | 565 | | | | 570 | | | | | 575 |
| Phe | Val | Pro | Thr | Arg | Ser | Tyr | Pro | Glu | Glu | Gly | Leu | Glu | Met | His | Pro |
| | | | 580 | | | | | 585 | | | | | 590 |
| Leu | Glu | Arg | Arg | Gly | Gly | His | His | Arg | Pro | Asp | Ser | Ser | Thr | Leu | His |
| | | 595 | | | | | 600 | | | | 605 |
| Thr | Asp | Asp | Gly | Tyr | Met | Pro | Met | Ser | Pro | Gly | Val | Ala | Pro | Val | Pro |
| | 610 | | | | | 615 | | | | 620 |
| Ser | Gly | Arg | Lys | Gly | Ser | Gly | Asp | Tyr | Met | Pro | Met | Ser | Pro | Lys | Ser |
| 625 | | | | 630 | | | | 635 | | | | | 640 |
| Val | Ser | Ala | Pro | Gln | Gln | Ile | Ile | Asn | Pro | Ile | Arg | Arg | His | Pro | Gln |
| | | | 645 | | | | 650 | | | | 655 |
| Arg | Val | Asp | Pro | Asn | Gly | Tyr | Met | Met | Met | Ser | Pro | Ser | Gly | Gly | Cys |
| | | | 660 | | | | 665 | | | | 670 |
| Ser | Pro | Asp | Ile | Gly | Gly | Gly | Pro | Ser | Ser | Ser | Ser | Ser | Ser | Ser | Asn |
| | | 675 | | | | 680 | | | | 685 |
| Ala | Val | Pro | Ser | Gly | Thr | Ser | Tyr | Gly | Lys | Leu | Trp | Thr | Asn | Gly | Val |
| | | 690 | | | 695 | | | | 700 |
| Gly | Gly | His | His | Ser | His | Val | Leu | Pro | His | Pro | Lys | Pro | Pro | Val | Glu |
| 705 | | | | | 710 | | | | 715 | | | | | 720 |
| Ser | Ser | Gly | Gly | Lys | Leu | Leu | Pro | Cys | Thr | Gly | Asp | Tyr | Met | Asn | Met |
| | | | | 725 | | | | | 730 | | | | | 735 |
| Ser | Pro | Val | Gly | Asp | Ser | Asn | Thr | Ser | Ser | Pro | Ser | Asp | Cys | Tyr | Tyr |
| | | | 740 | | | | 745 | | | | 750 |
| Gly | Pro | Glu | Asp | Pro | Gln | His | Lys | Pro | Val | Leu | Ser | Tyr | Tyr | Ser | Leu |
| | | 755 | | | | 760 | | | | 765 |
| Pro | Arg | Ser | Phe | Lys | His | Thr | Gln | Arg | Pro | Gly | Glu | Pro | Glu | Glu | Gly |
| | 770 | | | | 775 | | | | 780 |
| Ala | Arg | His | Gln | His | Leu | Arg | Leu | Ser | Thr | Ser | Ser | Gly | Gly | Leu | Leu |
| 785 | | | | | 790 | | | | 795 | | | | | 800 |
| Tyr | Ala | Ala | Thr | Ala | Asp | Asp | Ser | Ser | Ser | Ser | Thr | Ser | Ser | Asp | Ser |
| | | | | 805 | | | | 810 | | | | 815 |
| Leu | Gly | Gly | Gly | Tyr | Cys | Gly | Ala | Arg | Leu | Glu | Pro | Ser | Leu | Pro | His |
| | | | 820 | | | | 825 | | | | 830 |
| Pro | His | His | Gln | Val | Leu | Gln | Pro | His | Leu | Pro | Arg | Lys | Val | Asp | Thr |
| | | 835 | | | | 840 | | | | 845 |
| Ala | Ala | Gln | Thr | Asn | Ser | Arg | Leu | Ala | Arg | Pro | Thr | Arg | Leu | Ser | Leu |
| 850 | | | | | 855 | | | | 860 |
| Gly | Asp | Pro | Lys | Ala | Ser | Thr | Leu | Pro | Arg | Ala | Arg | Glu | Gln | Gln | Gln |
| 865 | | | | | 870 | | | | 875 | | | | | 880 |
| Gln | Gln | Gln | Pro | Leu | Leu | His | Pro | Pro | Glu | Pro | Lys | Ser | Pro | Gly | Glu |
| | | | | 885 | | | | 890 | | | | 895 |
| Tyr | Val | Asn | Ile | Glu | Phe | Gly | Ser | Asp | Gln | Ser | Gly | Tyr | Leu | Ser | Gly |
| | | | 900 | | | | 905 | | | | 910 |
| Pro | Val | Ala | Phe | His | Ser | Ser | Pro | Ser | Val | Arg | Cys | Pro | Ser | Gln | Leu |
| | | | 915 | | | | 920 | | | | 925 |
| Gln | Pro | Ala | Pro | Arg | Glu | Glu | Glu | Thr | Gly | Thr | Glu | Glu | Tyr | Met | Lys |
| | | 930 | | | | 935 | | | | 940 |
| Met | Asp | Leu | Gly | Pro | Gly | Arg | Arg | Ala | Ala | Trp | Gln | Glu | Ser | Thr | Gly |
| 945 | | | | | 950 | | | | 955 | | | | | 960 |
| Val | Glu | Met | Gly | Arg | Leu | Gly | Pro | Ala | Pro | Arg | Ala | Ala | Ser | Ile |
| | | | | 965 | | | | 970 | | | | 975 |
| Cys | Arg | Pro | Thr | Arg | Ala | Val | Pro | Ser | Ser | Arg | Gly | Asp | Tyr | Met | Thr |

|     |     |     |     |     |     |     | 980 |     |     |     |     | 985 |     |     |     |     |     | 990 |     |
|-----|-----|-----|-----|-----|-----|-----|-----|-----|-----|-----|-----|-----|-----|-----|-----|-----|-----|-----|-----|

Met Gln Met Ser Cys Pro Arg Gln Ser Tyr Val Asp Thr Ser Pro Ala
                995                             1000                        1005

Ala Pro Val Ser Tyr Ala Asp Met Arg Thr Gly Ile Ala Ala Glu Glu
    1010                        1015                        1020

Val Ser Leu Pro Arg Ala Thr Met Ala Ala Ser Ser Ser Ser Ser Ala
1025                    1030                        1035                    1040

Ala Ser Ala Ser Pro Thr Gly Pro Gln Gly Ala Ala Glu Leu Ala Ala
                1045                        1050                        1055

His Ser Ser Leu Leu Gly Gly Pro Gln Gly Pro Gly Gly Met Ser Ala
                1060                        1065                        1070

Phe Thr Arg Val Asn Leu Ser Pro Asn Arg Asn Gln Ser Ala Lys Val
            1075                        1080                        1085

Ile Arg Ala Asp Pro Gln Gly Cys Arg Arg Arg His Ser Ser Glu Thr
            1090                        1095                        1100

Phe Ser Ser Thr Pro Ser Ala Thr Arg Val Gly Asn Thr Val Pro Phe
1105                        1110                        1115                    1120

Gly Ala Gly Ala Ala Val Gly Gly Gly Gly Ser Ser Ser Ser Ser Ser
                    1125                        1130                        1135

Glu Asp Val Lys Arg His Ser Ser Ala Ser Phe Glu Asn Val Trp Leu
                1140                        1145                        1150

Arg Pro Gly Glu Leu Gly Gly Ala Pro Lys Glu Pro Ala Lys Leu Cys
            1155                        1160                        1165

Gly Ala Ala Gly Gly Leu Glu Asn Gly Leu Asn Tyr Ile Asp Leu Asp
        1170                        1175                        1180

Leu Val Lys Asp Phe Lys Gln Cys Pro Gln Glu Cys Thr Pro Glu Pro
1185                        1190                        1195                    1200

Gln Pro Pro Pro Pro Pro Pro His Gln Pro Leu Gly Ser Gly Glu
                    1205                        1210                        1215

Ser Ser Ser Thr Arg Arg Ser Ser Glu Asp Leu Ser Ala Tyr Ala Ser
                1220                        1225                        1230

Ile Ser Phe Gln Lys Gln Pro Glu Asp Arg Gln
        1235                        1240

(2) INFORMATION FOR SEQ ID NO:3:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CCNGG                                                                                                           5

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GCTCAGCGTT GGTGGTGGCG GTGG                                                   24

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GCCCGCTTGT TGATGTTGAA GCAGC    25

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GAAGTGGCGG CACAAGTCGA GCGC    24

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCAGCCTCAC CAAGGCCGGA GC    22

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ACCGTGCTAA GGGCCACCAC GACG    24

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGCACCACGG CCGCTGCCTC C    21

( 2 ) INFORMATION FOR SEQ ID NO:10:

( i ) SEQUENCE CHARACTERISTICS:
        ( A ) LENGTH: 23 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:10:

TCTACCGCCT TTGCCTGACC AGC  23

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:11:

GCAGTTGGAC GAGGACTGGC  20

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:12:

ACCATCCTGG AGGCCATGCG G  21

(2) INFORMATION FOR SEQ ID NO:13:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

AGGGCTGCCG TCCACCGAGG CTGG  24

(2) INFORMATION FOR SEQ ID NO:14:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:14:

CAGGCTCCTT CCGTGTCCGC G  21

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:15:

GAAGCACTAG ATCGCCGTGG G 21

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CTGTCGTCCA GTAGCACCAG TGG 23

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GACCGTTGGG GGCGGTCAGG G 21

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

GCGGTGAGGA GGAGCTAAGC 20

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

GCCACTGAGG ACTGGGACGG G 21

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

AGAGAACTCA CTCGGCAGGC 20

( 2 ) INFORMATION FOR SEQ ID NO:21:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:21:

GGCATGTAGC CATCATCCGT GTGG    24

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:22:

ACCCCTTGGA GCGTCGGGGG    20

( 2 ) INFORMATION FOR SEQ ID NO:23:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:23:

GCTGGGGCCA CCTCCTAAGT CAGG    24

( 2 ) INFORMATION FOR SEQ ID NO:24:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:24:

CAGAGAGTGG ACCCCAATGG    20

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:25:

GGCTGCTGGT GTTGGAGTCC    20

( 2 ) INFORMATION FOR SEQ ID NO:26:

( i ) SEQUENCE CHARACTERISTICS:
    ( A ) LENGTH: 20 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:26:

TCTTGCCTCA CCCCAAACCC 20

(2) INFORMATION FOR SEQ ID NO:27:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:27:

ATAGAGAAGG CGACCAGAGC 20

(2) INFORMATION FOR SEQ ID NO:28:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:28:

GAGCCGGAGG AGGGTGCCCG 20

(2) INFORMATION FOR SEQ ID NO:29:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:29:

AGGTAAGGTG CTGGCCTTGG 20

(2) INFORMATION FOR SEQ ID NO:30:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:30:

CAGACCAATA GCCGCCTGGC 20

(2) INFORMATION FOR SEQ ID NO:31:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:31:

TTCATGTACT CCTCAGTGCC 20

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

CTTCTGTCAG GTGTCCATCC 20

( 2 ) INFORMATION FOR SEQ ID NO:33:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

TGGCGAGGTG TCCACGTAGC 20

( 2 ) INFORMATION FOR SEQ ID NO:34:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

GGGCAGTGCC CAGCAGCCGG 20

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

CCAGCAGGGA CGAGTGGGCA GC 22

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

CCTCAGCAGC CTCTGCTTCC 20

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

CCACCGCCCC CTACTGCTGC 20

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

CCACACCCAG TGCCACCCGG 20

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

GAGGGCACTG TTTGAAGTCC 20

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

GAGCCAGCCA AACTGTGTGG 20

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

AACGACCTGC TGTGATGTCC 20